US012793852B2

(12) United States Patent
Ikemoto et al.

(10) Patent No.: US 12,793,852 B2
(45) Date of Patent: Nov. 10, 2026

(54) COMPUTER SYSTEM, METHOD, AND PROGRAM FOR ESTIMATING CONDITION OF SUBJECT

(71) Applicants: OSAKA UNIVERSITY, Suita (JP); NATIONAL HOSPITAL ORGANIZATION, Tokyo (JP)

(72) Inventors: Noriko Ikemoto, Suita (JP); Hajime Nagahara, Suita (JP); Satoru Tada, Suita (JP); Yu Moriguchi, Kawachinagano (JP)

(73) Assignees: OSAKA UNIVERSITY, Osaka (JP); NATIONAL HOSPITAL ORGANIZATION, Tokyo (JP)

( * ) Notice: Subject to any disclaimer, the term of this patent is extended or adjusted under 35 U.S.C. 154(b) by 294 days.

(21) Appl. No.: 18/568,055

(22) PCT Filed: Jun. 7, 2022

(86) PCT No.: PCT/JP2022/022989
§ 371 (c)(1),
(2) Date: Dec. 7, 2023

(87) PCT Pub. No.: WO2022/260046
PCT Pub. Date: Dec. 15, 2022

(65) Prior Publication Data

US 2024/0266053 A1 Aug. 8, 2024

(30) Foreign Application Priority Data

Jun. 7, 2021 (JP) ................................ 2021-095390

(51) Int. Cl.
*G16H 50/20* (2018.01)
*G16H 20/00* (2018.01)
*G16H 30/40* (2018.01)

(52) U.S. Cl.
CPC ............ *G16H 50/20* (2018.01); *G16H 20/00* (2018.01); *G16H 30/40* (2018.01)

(58) Field of Classification Search
None
See application file for complete search history.

(56) References Cited

U.S. PATENT DOCUMENTS

2021/0059569 A1 3/2021 Hiyama et al.
2021/0204836 A1 7/2021 Sankai
2021/0315486 A1* 10/2021 Delp ..................... G16H 50/50

FOREIGN PATENT DOCUMENTS

CN 112438724 A 3/2021
EP 3417777 A1 12/2018
(Continued)

OTHER PUBLICATIONS

T. T. Verlekar, et al., "Using transfer learning for classification of gait pathologies," 2018 IEEE International Conference on Bioinformatics and Biomedicine (BIBM), Madrid, Spain, 2018, pp. 2376-2381, doi: 10.1109/BIBM.2018.8621302. (Year: 2018).*
(Continued)

*Primary Examiner* — Devin C Hein
(74) *Attorney, Agent, or Firm* — Leydig, Voit & Mayer, Ltd.

(57) ABSTRACT

The present disclosure provides a computer system and the like for estimating a condition of a subject. In one embodiment, the present disclosure provides a computer system for estimating a condition of a subject, and the computer system includes a receiving means for receiving a plurality of images photographed of the subject walking, a generation means for generating at least one silhouette image of the subject from the plurality of images, and an estimation
(Continued)

means for estimating a condition related to at least one disease of the subject at least based on the at least one silhouette image.

21 Claims, 18 Drawing Sheets

(56) References Cited

FOREIGN PATENT DOCUMENTS

| | | | |
|---|---|---|---|
| JP | 2005-160747 | A | 6/2005 |
| JP | 2010-017447 | A | 1/2010 |
| JP | 2016-144598 | A | 8/2016 |
| JP | 2018-069035 | A | 5/2018 |
| JP | 2021-030051 | A | 3/2021 |
| WO | WO 2017/142082 | A1 | 8/2017 |

OTHER PUBLICATIONS

J. Loureiro et al., "Using a Skeleton Gait Energy Image for Pathological Gait Classification," 2020 15th IEEE International Conference on Automatic Face and Gesture Recognition (FG 2020), Buenos Aires, Argentina, 2020, pp. 503-507, doi: 10.1109/FG47880.2020.00064. (Year: 2020).*

Zhang, Qinglong et al., (2021). Group-CAM: Group Score-Weighted Visual Explanations for Deep Convolutional Networks. 10.48550/arXiv.2103.13859. (Year: 2021).*

Kalsi-Ryan, S. et al, . Quantitative Assessment of Gait Characteristics in Degenerative Cervical Myelopathy: A Prospective Clinical Study. J. Clin. Med. 2020, 9, 752. https://doi.org/10.3390/jcm9030752 (Year: 2020).*

S. Inui, F. Ren, S. Nishide and X. Kang, "Gait recognition in real environment using gait energy image generated by Mask R-CNN," 2020 IEEE International Conference on Mechatronics and Automation (ICMA), Beijing, China, 2020, pp. 1129-1133, doi: 10.1109/ICMA49215.2020.9233582. (Year: 2020).*

L. Lin, Y. Gao, K. Gong, M. Wang and X. Liang, "Graphonomy: Universal Image Parsing via Graph Reasoning and Transfer," in IEEE Transactions on Pattern Analysis and Machine Intelligence, vol. 44, No. 5, pp. 2504-2518, May 1, 2022, doi: 10.1109/TPAMI.2020.3043268. (Year: 2020).*

Zhao, J., Li, J., Liu, H. et al. Fine-Grained Multi-human Parsing. Int J Comput Vis 128, 2185-2203 (2020). https://doi.org/10.1007/s11263-019-01181-5 (Year: 2019).*

Studenski et al., "Gait Speed and Survival in Older Adults," *JAMA*, 305(1): 50-58 (2011).

Japan Patent Office, International Search Report in International Patent Application No. PCT/JP2022/022989 (Aug. 2, 2022).

* cited by examiner

FIG. 8A (a)

MS-G3D (skeleton)

| | Acc. | Sens. | Spec. |
|---|---|---|---|
| CV1 | 0.984 | 0.988 | 0.920 |
| CV2 | 0.986 | **1.000** | 0.801 |
| CV3 | 0.951 | 0.952 | 0.938 |
| Total | 0.974 | 0.981 | 0.880 |

(b)

ResNet50 (silhouette)

| | Acc. | Sens. | Spec. |
|---|---|---|---|
| CV1 | 0.985 | 0.987 | **0.940** |
| CV2 | 0.967 | 0.976 | 0.854 |
| CV3 | 0.975 | 0.973 | **1.000** |
| Total | 0.975 | 0.979 | 0.927 |

(c)

| Fusion | Acc. | Sens. | Spec. |
|---|---|---|---|
| CV1 | **0.996** | **1.000** | **0.940** |
| CV2 | **0.989** | 0.997 | **0.900** |
| CV3 | **1.000** | **1.000** | **1.000** |
| Total | **0.995** | **0.999** | **0.942** |

FIG. 8B

| lumbar vertebrae | accuracy | sensi-tivity | speci-ficity | false positive | false negative |
|---|---|---|---|---|---|
| skeleton | 0.968 | 0.976 | 0.869 | 0.024 | 0.131 |
| silhou-ette | 0.968 | 0.976 | 0.873 | 0.024 | 0.127 |
| fusion | 0.986 | 0.994 | 0.895 | 0.006 | 0.105 |

FIG. 8C

| cervical vertebrae | accuracy | sensi-tivity | speci-ficity | false positive | false negative |
|---|---|---|---|---|---|
| skeleton | 0.823 | 0.781 | 0.888 | 0.219 | 0.112 |
| silhou-ette | 0.818 | 0.776 | 0.883 | 0.224 | 0.117 |
| fusion | 0.854 | 0.775 | 0.976 | 0.225 | 0.024 |

(a)

(b)

COMPUTER SYSTEM, METHOD, AND PROGRAM FOR ESTIMATING CONDITION OF SUBJECT

TECHNICAL FIELD

The present disclosure relates to a computer system, method, and program for estimating a condition of a subject.

BACKGROUND ART

A wide variety of studies have been conducted on the close relationship between walking and health conditions (for example, Non-Patent Document 1).

PATENT DOCUMENTS

Non-Patent Documents (Non-patent Document 1) Studenski S. et al., "Gait Speed and Survival in Older Adults", JAMA. 2011, 305(1): 50-58, Journal of American Medical Association

SUMMARY OF THE INVENTION

Means for Solving Problem

In one aspect, the present disclosure provides a computer system, method, and program for estimating a condition of a subject from a plurality of images photographed of the subject walking.

In this aspect, the present disclosure provides, for example, the following.

(Item 1)

A computer system for estimating a condition of a subject, wherein the computer system comprises:

- a receiving means for receiving a plurality of images photographed of the subject walking,
- a generation means for generating at least one silhouette image of the subject from the plurality of images, and
- an estimation means for estimating a health-related condition of the subject at least based on the at least one silhouette image.

(Item 2)

The computer system according to item 1, wherein the estimation means estimates a condition including a condition related to at least one disease of the subject.

(Item 3)

The computer system according to item 1 or 2, wherein the estimation means estimates the condition by using a learned model that has learned the relationship between a learning silhouette image and the condition related to at least one disease of the subject shown in the learning silhouette image.

(Item 4)

The computer system according to any one of items 1 to 3, wherein

- the system further comprises an extraction means for extracting a skeletal feature of the subject from the plurality of images, and
- the estimation means estimates the condition further based on the skeletal feature.

(Item 5)

The computer system according to item 4, wherein the estimation means

- obtains a first score indicating the condition based on the at least one silhouette image,

- obtains a second score indicating the condition based on the skeletal feature, and
- estimates the condition based on the first score and the second score.

(Item 6)

The computer system according to any one of items 1 to 5, wherein the generation means generates the at least one silhouette image by

- extracting a plurality of silhouette regions from the plurality of images,
- normalizing each of the plurality of extracted silhouette regions, and
- averaging the plurality of normalized silhouette regions.

(Item 7)

The computer system according to any one of items 1 to 6, wherein the plurality of images are a plurality of frames in a video of the subject walking photographed from a direction approximately perpendicular to the direction in which the subject walks.

(Item 8)

The computer system according to any one of items 1 to 7, further comprising

- an analysis means for analyzing a result of the estimation by the estimation means, the analysis means identifying, in the at least one silhouette image, a region of interest that contributes relatively largely to the result of the estimation, and
- a modification means for modifying the algorithm of the estimation means based on the region of interest.

(Item 9)

The computer system according to any one of items 1 to 8, wherein the health-related condition includes a condition related to at least one disease of the subject, and the at least one disease includes a disease that causes a walking disorder.

(Item 10)

The computer system according to item 9, wherein the at least one disease includes at least one selected from the group consisting of locomotor diseases that cause a walking disorder, neuromuscular diseases that cause a walking disorder, cardiovascular disease that cause a walking disorder, and respiratory diseases that cause a walking disorder.

(Item 11)

The computer system according to item 9, wherein estimating the condition related to at least one disease includes determining which organ the disease causing a walking disorder relates to.

(Item 12)

The computer system according to item 11, wherein the determination includes determining whether the disease causing a walking disorder is a locomotor disease, a neuromuscular disease, a circulatory system disease, or a respiratory disease.

(Item 13)

The computer system according to any one of items 9 to 12, wherein the at least one disease includes at least one selected from the group consisting of cervical spondylotic myelopathy (CSM), lumbar canal stenosis (LCS), osteoarthritis (OA), neuropathy, intervertebral disc herniation, ossification of the posterior longitudinal ligament (OPLL), rheumatoid arthritis (RA), heart failure, hydrocephalus, peripheral artery disease (PAD), myositis, myopathy, Parkinson's disease, amyotrophic lateral sclerosis (ALS), spinocerebellar degeneration, multiple system atrophy, brain tumor, Lewy body dementia, subclinical fracture, drug addiction, meniscal injury, ligament injury, spinal cord infarction, myelitis, myelopathy, pyogenic spondylitis, discitis, bunion, chronic obstructive pulmonary disease (COPD), obesity, cerebral infarction, locomotive syndrome, frailty, and hereditary spastic paraplegia.

(Item 14)

The computer system according to any one of items 1 to 12, wherein the health-related condition of the subject is represented by the severity of at least one disease, and the estimation means estimates the severity.

(Item 15)

The computer system according to item 14, wherein the disease is cervical spondylotic myelopathy, and the estimation means estimates a cervical JOA score as the severity.

(Item 16)

The computer system according to item 15, wherein the receiving means receives a plurality of images photographed of walking of a subject whose cervical JOA score is determined to be 10 or more.

(Item 17)

The computer system according to item 1, wherein the estimation means estimates the walking ability of the subject.

(Item 18)

The computer system according to item 17, wherein the walking condition of the subject is represented by a numerical value indicating which age level the subject is at.

(Item 19)

The computer system according to any one of items 1 to 18, further comprising a providing means for providing treatment or intervention or information according to the estimated condition.

(Item 20)

A method for estimating a condition of a subject, wherein the method comprises:

receiving a plurality of images photographed of the subject walking, generating at least one silhouette image of the subject from the plurality of images, and estimating a health-related condition of the subject at least based on the at least one silhouette image.

(Item 20A)

The method according to item 20, comprising the feature or features described in one or more of the above items.

(Item 21)

A program for estimating a condition of a subject, wherein the program is executed in a computer comprising a processor, and the program causes the processor to perform processing including:

receiving a plurality of images photographed of the subject walking, generating at least one silhouette image of the subject from the plurality of images, and estimating a health-related condition of the subject at least based on the at least one silhouette image.

(Item 21A)

The program according to item 21, comprising the feature or features described in one or more of the above items.

(Item 21B)

A storage medium that stores a program for estimating a condition of a subject, wherein the program is executed in a computer comprising a processor, and the program causes the processor to perform processing including:

receiving a plurality of images photographed of the subject walking, generating at least one silhouette image of the subject from the plurality of images, and estimating a health-related condition of the subject at least based on the at least one silhouette image.

(Item 21C)

The storage medium according to item 21B, comprising the feature or features described in one or more of the above items.

(Item 22)

A method that creates a model for estimating a condition of a subject, wherein the method comprises:

receiving a plurality of images photographed of the object walking, generating at least one silhouette image of the object from the plurality of images, and causing a machine learning model to learn the at least one silhouette image as input training data and the health-related condition of the object as output training data, for each object among a plurality of objects.

(Item 22A)

The method according to item 22, comprising the feature or features described in one or more of the above items.

(Item 22B)

A system that creates a model for estimating a condition of a subject, wherein the system comprises:

a receiving means for receiving a plurality of images photographed of the object walking, a generation means for generating at least one silhouette image of the object from the plurality of images, and a learning means for causing a machine learning model to learn the at least one silhouette image as input training data and the condition related to at least one disease of the object as output training data.

(Item 22C)

The system according to item 22B, comprising the feature or features described in one or more of the above items.

(Item 22D)

A program that creates a model for estimating a condition of a subject, wherein the program is executed in a computer comprising a processor, and the program causes the processor to perform processing including:

receiving a plurality of images photographed of the object walking, generating at least one silhouette image of the object from the plurality of images, and causing a machine learning model to learn the at least one silhouette image as input training data and the condition related to at least one disease of the object as output training data, for each object among a plurality of objects.

(Item 22E)

The program according to item 22D, comprising the feature or features described in one or more of the above items.

(Item 22F)

A storage medium that stores a program that creates a model for estimating a condition of a subject, wherein the program is executed in a computer comprising a processor, and the program causes the processor to perform processing including:

receiving a plurality of images photographed of the object walking, generating at least one silhouette image of the object from the plurality of images, and causing a machine learning model to learn the at least one silhouette image as input training data and the condition related to at least one disease of the object as output training data, for each object among a plurality of objects.

(Item 22G)

The storage medium according to item 22F, comprising the feature or features described in one or more of the above items.

(Item 23)

A method for treating, preventing, or improving a health condition, disorder, or disease in a subject, wherein the method comprises:

(A) receiving a plurality of images photographed of the subject walking, (B) generating at least one silhouette image of the subject from the plurality of images, (C) estimating a health-related condition of the subject at least based on the at least one silhouette image, (D) calculating a method for treatment, prevention, or improvement to be applied to the subject based on the health-related condition of the subject, (E) administering the method for treatment, prevention, or improvement to the subject, and (F) repeating the steps (A) to (E) as necessary.

(Item 23A)

A system that treats, prevents, or improves a health condition, disorder, or disease of a subject, wherein the system comprises:

(A) a receiving means for receiving a plurality of images photographed of the subject walking, (B) a generation means for generating at least one silhouette image of the subject from the plurality of images, (C) an estimation means for estimating a health-related condition of the subject at least based on the at least one silhouette image, (D) a calculation means for calculating a method for treatment, prevention, or improvement to be applied to the subject based on the health-related condition of the subject, and (E) a means for administering the method for treatment, prevention, or improvement to the subject.

(Item 23B)

A program for treating, preventing, or improving a health condition, disorder, or disease of a subject, wherein the program is executed on a computer comprising a processor, and the program causes the processor to perform processing including:

(A) receiving a plurality of images photographed of the subject walking, (B) generating at least one silhouette image of the subject from the plurality of images, (C) estimating a health-related condition of the subject at least based on the at least one silhouette image, (D) calculating a method for treatment, prevention, or improvement to be applied to the subject based on the health-related condition of the subject, (E) administering the method for treatment, prevention, or improvement to the subject, and (F) repeating the steps (A) to (E) as necessary.

(Item 23C)

A storage medium that stores a program for treating, preventing, or improving a health condition, disorder, or disease of a subject, wherein the program is executed in a computer comprising a processor, and the program causes the processor to perform processing including:

(A) receiving a plurality of images photographed of the subject walking, (B) generating at least one silhouette image of the subject from the plurality of images, (C) estimating a health-related condition of the subject at least based on the at least one silhouette image, (D) calculating a method for treatment, prevention, or improvement to be applied to the subject based on the health-related condition of the subject, (E) administering the method for treatment, prevention, or improvement to the subject, and (F) repeating the steps (A) to (E) as necessary.

Effect of the Invention

According to the present disclosure, it is possible to provide a computer system, method and program for estimating a condition of a subject, capable of estimating a condition related to at least one medical condition such as a disease, disorder, syndrome, symptom or the like of the subject with high accuracy. Furthermore, according to the present disclosure, it may be possible to identify even diseases that cannot be identified just by observing the walking behavior by a doctor.

BRIEF DESCRIPTION OF DRAWINGS

FIG. 8A is a diagram showing the results of Example 1.

FIG. 8B is a diagram showing the results of Example 2.

FIG. 8C is a diagram showing the results of Example 3.

DESCRIPTION OF EMBODIMENTS

Figure 1:
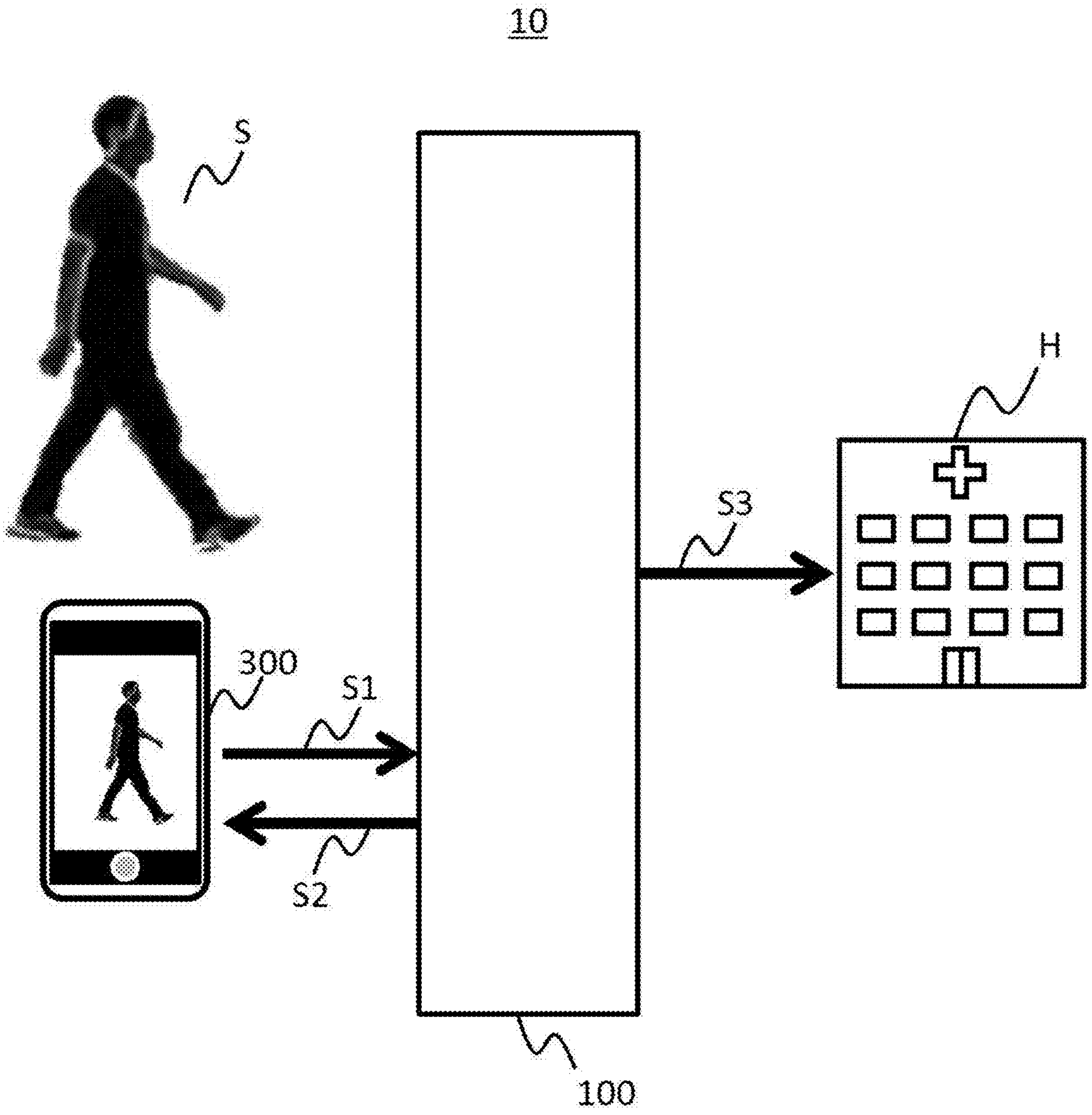
FIG. 1 is a diagram showing an example of a flow 10 for estimating a condition of a subject from a walking video of the subject using an embodiment of the present disclosure.

The present disclosure will be described below. Throughout this specification, references to the singular should be understood to include the plural unless specifically stated otherwise. Accordingly, singular articles (e.g., "a", "an", "the", etc. in English) should be understood to also include the plural concept, unless specifically stated otherwise. Further, it should be understood that the terms used herein have the meanings commonly used in the art unless otherwise specified. Accordingly, unless defined otherwise, all technical and scientific terms used herein have the same meaning as commonly understood by one of ordinary skill in the art to which this invention belongs. In case of conflict, the present specification (including definitions) will control.

Definitions

In the present specification, "subject" refers to any person or animal objected by the technology of the present disclosure. "Subject" may be used synonymously with "object" or patient.

In the present specification, the "condition" of a "subject" refers to the condition of the subject's body or mind.

In the present specification, "walking" refers to any movement (exercise) performed by an animal with limbs (e.g., feet (legs), arms, etc.) using the limbs. "Walking" includes running (i.e., an action in which all feet leave the ground at the same time), moving on all fours (so-called crawling), and the like, in addition to walking in the narrow sense (i.e., an action in which all feet do not leave the ground at the same time).

In the present specification, "walking disorder" refers to any disorder in walking, and is characterized by an abnormality in the way the subject's body moves (that is, the displacement of the entire body) or the displacement of each part of the body while walking.

In the present specification, the term "disease" refers to a condition in which an object condition is unwell or inconvenient. "Disease" is sometimes used synonymous with the terms "disorder" (a condition that interferes with normal functioning), "symptom" (an abnormal condition in an object), "syndrome" (a condition in which several symptoms occur), and the like. In particular, diseases that cause abnormalities in the way a subject's body moves or the displacement of various parts of the body while walking are referred to as "diseases that cause a walking disorder", and diseases that cause a walking disorder include diseases that are classified and expressed by organ, such as "locomotor diseases that cause a walking disorder", "neuromuscular diseases that cause a walking disorder", "cardiovascular disease that cause a walking disorder", "respiratory diseases that cause a walking disorder", and the like.

In the present specification, "locomotor diseases that cause a walking disorder" refer to diseases related to bone and joint function that cause a walking disorder, and include, but not limited to, for example, osteoarthritis (OA), rheumatoid arthritis, meniscus injury, ligament injury, locomotive syndrome, cervical spondylotic myelopathy (CSM), lumbar canal stenosis (LCS), ossification of the posterior longitudinal ligament (OPLL), intervertebral disc herniation, and discitis. Cervical spondylotic myelopathy (CSM), lumbar canal stenosis (LCS), ossification of the posterior longitudinal ligament (OPLL), intervertebral disc herniation, and discitis can also be "neuromuscular diseases that cause a walking disorder", which will be described later.

In the present specification, "neuromuscular diseases that cause a walking disorder" refer to diseases related to nerve and muscle functions that cause a walking disorder, and include, but not limited to, for example, cervical spondylotic myelopathy (CSM), lumbar canal stenosis (LCS), intervertebral disc herniation, spinocerebellar degeneration, multiple system atrophy, neuropathy, hydrocephalus, myositis, myopathy, amyotrophic lateral sclerosis (ALS), brain tumor, spinal cord infarction, myelitis, myelopathy, ossification of the posterior longitudinal ligament (OPLL), discitis, Parkinson's disease, cerebral infarction, and hereditary spastic paraplegia. Cervical spondylotic myelopathy (CSM), lumbar canal stenosis (LCS), ossification of the posterior longitudinal ligament (OPLL), intervertebral disc herniation, and discitis can also be the aforementioned "locomotor diseases that cause a walking disorder."

In the present specification, "cardiovascular disease that cause a walking disorder" refer to diseases related to heart and blood vessel function that cause a walking disorder, and include, but not limited to, for example, heart failure, peripheral artery disease (PAD), and frailty.

In the present specification, "respiratory diseases that cause a walking disorder" refer to diseases related to lung function that cause a walking disorder, and include, but not limited to, for example, chronic obstructive pulmonary disease (COPD).

In this specification, the "silhouette image" of a subject, etc. means an image that represents the area of the subject, etc. by representing pixels that belong to the subject, etc. in the image and pixels that do not belong to the subject, etc. with different pixel values. Typically, the "silhouette image of a subject, etc." may be a binary image in which all pixels belonging to the subject, etc. in the image are set to the same value, and all pixels not belonging to the subject, etc. are set to the same value. In another example, it may be a multi-valued image in which the subject, etc. in the image is divided into multiple parts (for example, by region), all pixels belonging to the same part are set to the same value, and all pixels that do not belong to the subject, etc. are set to the same value. In another example, it may be a multi-valued image in which the subject, etc. in the image is divided into multiple parts (for example, by region), all pixels belonging to the same part are set to the same value, the part that does not belong to the subject, etc. is divided into multiple parts, all pixels belonging to the same part are set to the same value, and each pixel value is a value that allows discrimination between a portion belonging to the subject and a portion not belonging to the subject.

In this specification, "skeletal feature of a subject" refers to a feature that can represent the skeleton of a subject. The skeletal feature includes, for example, the positions and angles of multiple joints of the subject. In one example, the skeletal feature may be represented by a graph structure in which a plurality of joints of the subject are represented by points (keypoints) and the points are connected. As such graph structures, COCO having 18 keypoints and Body 25 having 25 keypoints are known. In general, the more Keypoints there are, the higher the accuracy of representing the subject's skeleton.

In this specification, "estimate the condition" may be a concept that includes estimating the future condition in addition to estimating the current condition.

In the present specification, "treatment" includes conservative treatment and surgical treatment. The conservative treatment includes drug treatment and rehabilitation treatment, and the rehabilitation includes physical therapy and occupational therapy. The rehabilitation treatment includes rehabilitation treatment with face-to-face instruction and rehabilitation treatment with remote instruction.

In the present specification, "about" means ±10% of the following numerical value.

Preferred Embodiment

Preferred embodiments of the present disclosure will be described below. It is understood that the embodiments provided below are provided for a better understanding of the present disclosure, and the scope of the present disclosure should not be limited to the following description. Therefore, it is clear that those skilled in the art can take the description in this specification into account and make appropriate modifications within the scope of the present disclosure. It is also understood that the following embodiments can be used alone or in combination.

Hereinafter, preferred embodiments of the present disclosure will be described with reference to the drawings.

1. Flow for Estimating Condition of Subject From Walking Video of Subject

FIG. 1 shows an example of a flow 10 for estimating a condition of a subject from a walking video of the subject using an embodiment of the present disclosure. Flow 10 is such that the disease-related condition of the subject S is estimated only by taking the subject S walking with a terminal device 300, and the estimated result is provided to a doctor or the subject S. Thereby, the subject S can easily know whether or not the subject has a disease. In addition, the doctor can use the estimated results in diagnosing the subject S, which can improve the accuracy of diagnosis.

First, the subject S uses a terminal device 300 (for example, a smartphone, a tablet, etc.) to photograph a video of himself walking. Note that since a video can be considered to be a plurality of consecutive images (still images), in this specification, a "video" is used synonymously with a "a plurality of images" or a "multiple continuous images." Note that the subject S walking may be photographed not by the terminal device 300 but by a photographing means such as a digital camera or a video camera.

For example, the subject S walking in a straight line on flat ground is photographed from the side, specifically, from a direction substantially orthogonal to the walking direction. At this time, for example, in order to be able to photograph steady walking of the subject S, it is preferable to photograph the subject S after having walked several meters, rather than at the beginning of the walk. For example, when the subject S is allowed to walk about 10 meters, it is preferable that a terminal device 300 or a photographing means is installed so that the subject walking for about 4 m in the middle, excluding the first about 3 m and the last about 3 m, can be appropriately photographed.

In step S1, the photographed video is provided to the server device 100. The manner in which the video is provided to the server device 100 does not matter. For example, the video may be provided to the server device 100 via a network (e.g., the Internet, LAN, etc.). For example, the video may be provided to the server device 100 via a storage medium (e.g., a removable medium).

Next, in the server device 100, processing is performed on the video provided in step S1. The server device 100 processes each of a plurality of frames in a video. Through processing by the server device 100, a disease condition of the subject S is estimated. For example, through processing by the server device 100, it can be estimated whether the subject S has a certain disease or does not have a certain disease. For example, through processing by the server device 100, the level (for example, mild, moderate, severe) of a certain disease that the subject S has can be estimated. Here, the disease is a disease that typically causes a walking disorder, and can be, for example, a locomotor disease that causes a walking disorder, a neuromuscular disease that causes a walking disorder, a circulatory disease that causes a walking disorder, or a respiratory disease that causes a walking disorder. More specifically, the disease includes, but not limited to, for example, cervical spondylotic myelopathy (CSM), lumbar canal stenosis (LCS), osteoarthritis (OA), neuropathy, intervertebral disc herniation, posterior longitudinal ligament bone OPLL, rheumatoid arthritis (RA), heart failure, hydrocephalus, peripheral artery disease (PAD), myositis, myopathy, Parkinson's disease, amyotrophic lateral sclerosis (ALS), spinocerebellar degeneration, multiple system atrophy, brain tumor, Lewy body dementia, subclinical fracture, drug addiction, meniscal injury, ligament injury, spinal cord infarction, myelitis, myelopathy, pyogenic spondylitis, discitis, bunion, chronic obstructive pulmonary disease (COPD), obesity (obesity is distinguished from fatness in that fatness is a state in which adipose tissue has accumulated excessively, and BMI is 25 $kg/m^2$ or more, while obesity is a disease that is associated with health disorders caused by or related to fatness, or is expected to be associated with the health disorders, and that medically requires weight loss.), cerebral infarction, locomotive syndrome, frailty, and hereditary spastic paraplegia. More preferably, the disease can be at least one of neuropathy, myositis, osteoarthritis (OA), rheumatoid arthritis (RA), heart failure, chronic obstructive pulmonary disease (COPD), and Parkinson's disease. In addition, such estimation may include determining which organ the disease causing a walking disorder relates to, and such determination may include determining whether the disease is a locomotor disease, a neuromuscular disease, a cardiovascular disease, or a respiratory disease.

In step S2, the result estimated by the server device 100 is provided to the subject S. The manner in which the estimated results are provided does not matter. For example, the estimated result may be provided from the server device 100 to the terminal device 300 via the network, may be provided to the subject S via a storage medium, or may also be provided to the subject S via a paper medium.

Thereby, the subject S can easily know whether the subject has a disease or the level of the subject's disease. At this time, for example, treatment or intervention depending on the disease state of the subject S may be provided to the subject S, or information depending on the disease condition of the subject S (for example, information that promotes behavioral change, information that supports rehabilitation) may be provided to the subject S.

In addition to or in place of step S2, the result estimated by the server device 100 is provided to the doctor, in step S3. The manner in which estimated results are provided does not matter. For example, the estimated results may be provided from the server device 100 to the terminal device of the hospital H via the network, may be provided to the doctor via a storage medium, or may be provided to the doctor via a paper medium.

Thereby, the doctor can utilize the estimated results for diagnosing whether or not the subject S has a disease or for diagnosing the level of the disease that the subject has. For example, even if a disease is difficult to diagnose or requires experience or knowledge to diagnose, it may be possible to diagnose it accurately using the estimated results. At this time, for example, information depending on a disease condition of the subject S (for example, information on recommended treatment or intervention, information on recommended rehabilitation) may be provided to the doctor.

In the example described above, the flow 10 has been explained in which the subject S can receive the estimated result of the disease condition of the subject S simply by photographing a video of the subject itself walking, but the present invention is not limited to this. For example, a flow is also possible in which the estimated results of subject S's disease condition will be provided to doctors, physical therapists, caregivers, family members of the subject S, or the like, only by the doctor using a camera to photograph a video of the subject S walking, or simply by having another person photograph a video of the subject walking using the terminal device 300.

For example, the server device 100 described above may be implemented as a server device that provides cloud services. The subject S or the doctor can access the server device 100 from a terminal device (for example, a smartphone, a personal computer) and receive the cloud service of receiving the estimated result of the disease condition of the subject S. For example, the subject S or the doctor may access the server device 100 via an application installed on a terminal device, or may access the server device 100 via a web application. Such cloud services can be provided to medical institutions or subjects both domestically and internationally. Applications for receiving provision of such cloud services can be provided to domestic and foreign medical institutions or subjects, for example, as medical devices or healthcare products. In the processing of estimating the disease condition of the subject S, the accuracy can be improved as more information from subjects is collected and learned, therefore, in order to improve the accuracy of the processing, the processing program for estimating the disease condition of the subject S may need to be updated frequently. By implementing the server device 100 as a server device that provides a cloud service, there is an advantage that the program for the processing of estimating the disease condition of the subject S can be easily updated.

Note that it is also possible for the terminal device 300 to perform the processing by the server device 100 described above. In this case, the server device 100 can be omitted and the terminal device 300 can operate standalone. Software that causes a processor to perform a processing of estimating the disease condition of the subject S may be installed in the terminal device 300. Such software can be provided to the subject S as a medical device or a healthcare product. In the above-described example in which the estimated result of the disease-related condition of subject S is provided to a doctor, physical therapist, caregiver, or family member of subject S, the estimated result can be provided from the terminal device 300 without going through the server device 100.

For example, it is also possible to perform the processing by the server device 100 described above on a terminal device at a medical institution. In this case, the server device 100 can be omitted and the terminal device can operate standalone. If the terminal device includes a camera, the terminal device 300 may also be omitted. Software that causes a processor to perform a processing of estimating the disease condition of the subject S may be installed in the terminal device. Such software can be provided as medical equipment to medical institutions both domestically and internationally. In this example, the estimation result may be provided from the terminal device to the terminal device of the doctor S or the terminal device 300 of the subject S, for example.

For example, it is also possible to perform the processing by the server device 100 described above using a dedicated device. In this case, the server device 100 and the terminal device 300 can be omitted, and the dedicated device can operate standalone. The dedicated device may include, for example, a camera, a processing unit, and a memory that stores software that causes the processing unit to perform a processing of estimating the disease condition of the subject S. Such dedicated equipment can be provided as medical equipment to medical institutions both domestically and internationally. In this example, the estimation result can be provided to the terminal device of the doctor S or the terminal device 300 of the subject S from the dedicated device, for example.

Note that although the above example describes estimating a condition related to a specific disease, the present disclosure is not limited thereto. For example, as a condition related to a disease, it may be estimated whether the person has some kind of disease, that is, whether the person is a healthy person or not. Furthermore, the present disclosure can estimate not only the disease-related condition of the subject but also the subject's health-related condition. For example, the present disclosure can similarly estimate whether the subject is in a healthy state, whether the subject is in a state where the subject does not have a disease but has signs of the disease (i.e., pre-disease), and what level of health the subject is at, and the level of walking ability of a subject, and the like.

The flow 10 described above can be realized using the computer system 100 of the present invention, which will be described later.

2. Configuration of Computer System for Estimating Condition of Subject

Figure 2:
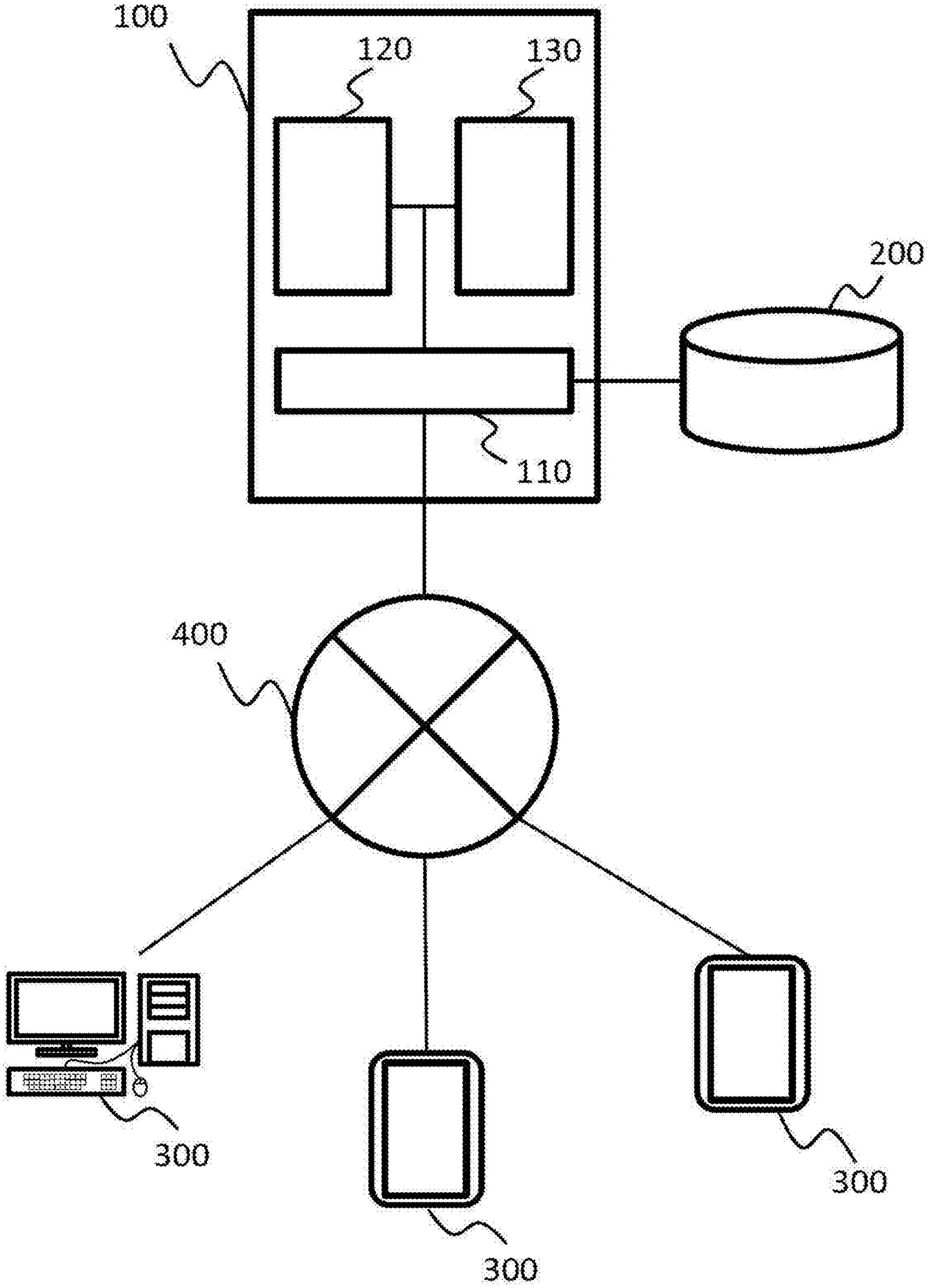
FIG. 2 is a diagram showing an example of the configuration of a computer system 100 for estimating a condition of a subject.

FIG. 2 shows an example of the configuration of a computer system 100 for estimating a condition of a subject.

In this example, the computer system 100 is connected to a database section 200. Further, the computer system 100 is connected to at least one terminal device 300 via a network 400.

Network 400 may be any type of network. Network 400 may be, for example, the Internet or a LAN. Network 400 may be a wired network or a wireless network.

An example of the computer system 100 is a server device, but is not limited thereto. The computer system 100 may be a terminal device (for example, a terminal device held by a subject, a terminal device installed in a hospital, a terminal device installed in a public place (for example, a community center, a government office, a library, etc.)), alternatively, it may be a dedicated device. An example of the terminal device 300 is a terminal device held by a subject, a terminal device installed in a hospital, or a terminal device installed in a public place (for example, a community center, government office, library, etc.), but the examples is not limited to this. Here, the server device and the terminal device may be any type of computer. For example, the terminal device can be any type of terminal device such as a smartphone, a tablet, a personal computer, smart glasses, etc. It is preferable that the terminal device 300 includes, for example, a photographing means such as a camera.

The computer system 100 includes an interface section 110, a processor section 120, and a memory section 130.

The interface section 110 exchanges information with the outside of the computer system 100. The processor section 120 of the computer system 100 can receive information from outside the computer system 100 via the interface section 110, and can send information to the outside of the computer system 100. The interface section 110 can exchange information in any format.

The interface section 110 includes, for example, an input section that allows information to be input into the computer system 100. It does not matter in what manner the input section allows information to be input into the computer system 100. For example, if the input section is a receiver, the input may be performed by the receiver receiving information from outside the computer system 100 via the network 400. Alternatively, if the input section is a data reading device, the information may be input by reading the information from a storage medium connected to the computer system 100. Alternatively, for example, if the input section is a touch panel, the user may input information by touching the touch panel. Alternatively, if the input section is a mouse, the user may input information by operating the mouse. Alternatively, if the input section is a keyboard, the user may input information by pressing keys on the keyboard. Alternatively, if the input section is a microphone, the information may be input by the user inputting voice into the microphone. Alternatively, if the input section is a camera, information photographed by the camera may be input.

For example, the input section makes it possible to input a video photographed of a subject walking into the computer system 100.

The interface section 110 includes, for example, an output section that allows information to be output from the computer system 100. It does not matter in what manner the output section allows information to be output from the computer system 100. For example, if the output section is a transmitter, the transmitter may output the information by transmitting it to the outside of the computer system 100 via the network 400. Alternatively, for example, if the output section is a data writing device, the information may be output by writing the information to a storage medium connected to the computer system 100. Alternatively, if the output section is a display screen, the information may be output to the display screen. Alternatively, if the output section is a speaker, the information may be output by voice from the speaker.

For example, the output section can output the condition of the subject estimated by the computer system 100 to the outside of the computer system 100.

The processor section 120 executes processing of the computer system 100 and controls the overall operation of the computer system 100. The processor section 120 reads a program stored in the memory section 130 and executes the program. This allows the computer system 100 to function as a system that executes desired steps. The processor section 120 may be implemented by a single processor or by multiple processors.

The memory section 130 stores programs required to execute the processing of the computer system 100, data required to execute the programs, and the like. The memory section 130 may store a program for processing for estimating a condition of a subject (for example, a program that implements the processing shown in FIG. 6A or FIG. 6B, which will be described later) and/or a program for processing for creating a model for estimating a condition of a subject (for example, a program that implements the processing shown in FIG. 7A or FIG. 7B, which will be described later). Here, it does not matter how the program is stored in the memory section 130. For example, the program may be preinstalled in the memory section 130. Alternatively, the program may be installed in the memory section 130 by being downloaded via a network. Alternatively, the program may be stored on a computer-readable storage medium.

The database section 200 may store, for example, a plurality of images photographed of each of a plurality of objects walking. The plurality of images may be, for example, images transmitted from each object terminal device 300 to the database section 200 (via the computer system 100), or may be images photographed by a camera that the computer system 100 may include. For example, a plurality of images photographed of a plurality of objects walking may be stored in association with the disease condition of each object. The data stored in the database section 200 can be used, for example, to create a model for estimating the condition of the subject.

The database section 200 may store a plurality of images photographed of a subject walking as a prediction object. The plurality of images may be, for example, those transmitted from the terminal device 300 of the subject as a prediction object to the database section 200 (via the computer system 100), or may be, for example, those photographed by a camera that the computer system 100 may include.

Further, the database section 200 may store, for example, the estimation results of the subject's condition output by the computer system 100.

In the example shown in FIG. 2, the database section 200 is provided outside the computer system 100, but the present invention is not limited thereto. It is also possible to provide at least a portion of the database section 200 inside the computer system 100. At this time, at least a part of the database section 200 may be implemented by the same storage unit as the storage unit that implements the memory section 130, or may be implemented by a storage unit that is different from the storage unit that implements the memory section 130. In any case, at least part of the database section 200 is configured as a storage unit for the computer system 100. The configuration of the database section 200 is not limited to a specific hardware configuration. For example, the database section 200 may be composed of a single hardware component or a plurality of hardware components. For example, the database section 200 may be configured as an external hard disk device of the computer system 100, or may be configured as a storage on a cloud connected via a network.

Figure 3A:
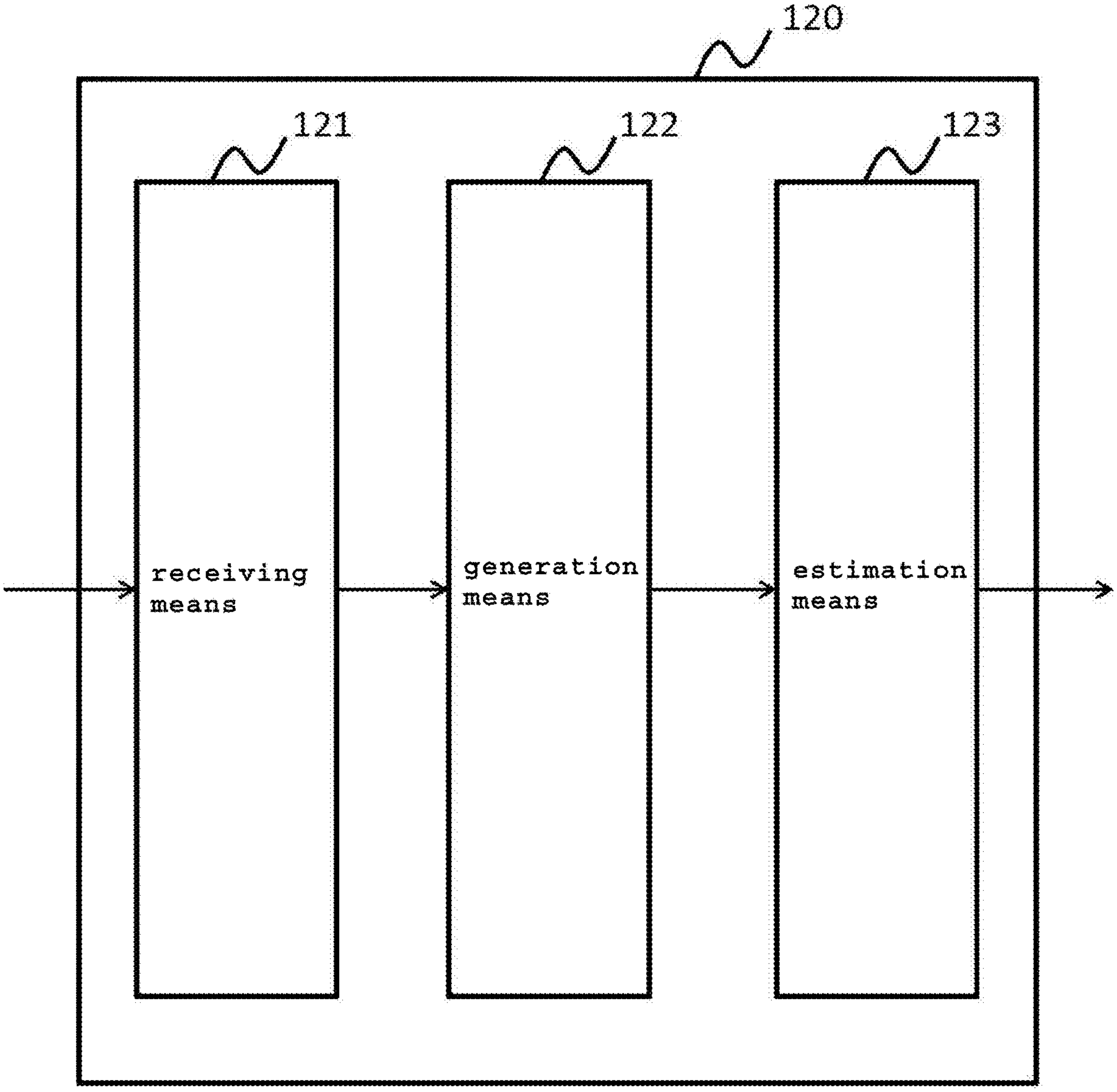
FIG. 3A is a diagram showing an example of the configuration of a processor section 120 in an embodiment.

FIG. 3A shows an example of the configuration of the processor section 120 in one embodiment.

The processor section 120 includes a receiving means 121, a generation means 122, and an estimation means 123.

The receiving means 121 is configured to receive a plurality of images photographed of the subject walking. The receiving means 121 can receive a plurality of images from outside the computer system 100 via the interface section 110. The plurality of images may be, for example, images transmitted from the subject's terminal device 300 to the computer system 100, or images stored in the database section 200 and transmitted from the database section 200 to the computer system 100.

The plurality of images may be, for example, a plurality of images photographed by continuously photographing still images, or a plurality of frames forming a video. The plurality of images may have any frame rate, but preferably the frame rate may be between 20 fps and 60 fps, more preferably 30 fps.

The plurality of images received by the receiving means 121 are provided to the generation means 122.

The generation means 122 is configured to generate a silhouette image of the subject from an image of the subject. The generation means 122 can generate at least one silhouette image from the plurality of images received by the receiving means 121, for example. The generation means 122 can generate the silhouette image using techniques known in the technical field. The generation unit 122 can generate the silhouette image using, for example, a technique called graph transfer learning or semantic segmentation. Specific examples of the silhouette image generation method using graph transfer learning include, but not limited to, a method using Graphonomy (https://arxiv.org/abs/1904.04536).

For example, the generation means 122 may generate the silhouette image as a binary image in which all pixels belonging to the subject in the image have the same value and all pixels not belonging to the subject have the same value, or may generate the silhouette image as a multivalued image in which the subject in the image is divided into multiple parts (for example, by body part), and all pixels belonging to the same part have the same value, and all pixels that do not belong to the subject have the same value. For example, according to the Graphonomy described above, a silhouette image can be generated as a multivalued image in which each part of the subject is represented by a different pixel value. In the silhouette image as a multivalued image, by representing all parts with the same pixel value, it is possible to generate a silhouette image as a binary image.

In one example, the generation unit 122 may generate N silhouette images from N images, or may generate M silhouette images from N images (N≥2, N>M or N<M). In a particular example, the generation means 122 may generate one silhouette image from N images.

For example, the generation unit 122 can generate M silhouette images from N images (N>M). At this time, the generating means 122 can generate M average silhouette images by generating a silhouette image from each of the N images and averaging at least some of the generated N silhouette images. Preferably, one average silhouette image can be generated by averaging all N silhouette images.

At this time, for example, the generating means 122 can generate M, preferably one silhouette image, by extracting N silhouette regions from N images, normalizing the extracted N silhouette regions, and averaging the N normalized silhouette regions.

Here, the normalization processing may be performed, for example, based on the height of the subject in the image. Normalization is performed, for example, by extracting a silhouette region of the subject from each of a plurality of silhouette images, and resizing (that is, enlarging or reducing) the plurality of extracted silhouette regions based on the height of the subject. In one example, normalization is done by resizing the subject's silhouette region such that the vertical length of the silhouette region is approximately 32 pixels, approximately 64 pixels, approximately 128 pixels, approximately 256 pixels, approximately 512 pixels, etc. At this time, the horizontal length may be determined to maintain the aspect ratio, or may be a fixed value, such as about 22 pixels, about 44 pixels, about 88 pixels, about 176 pixels, about 352 pixels, etc. Preferably, the aspect ratio is maintained. The larger the size of the silhouette image, the higher the calculation cost, and the smaller the size of the silhouette image, the more the feature amount is lost, therefore, it is preferable to determine the size of the normalized silhouette image while considering this trade-off when. The size of the silhouette image after normalization may preferably be 128×88 (length×width). This is because if length×width=128×88, sufficient accuracy can be obtained with relatively low calculation cost. The normalization may preferably be to normalize the silhouette region in the vertical direction based on the subject's height so that the aspect ratio is maintained, and to generate a silhouette image of length×width=128×88.

In the normalization process, for example, in order to reduce the influence of noise and the like, smoothing processing may be additionally performed so that the movement of the center of gravity of the silhouette becomes smooth.

The averaging processing may be performed, for example, by averaging the pixel values of each pixel in N silhouette regions.

In the example described above, the value of N may be any integer greater than or equal to 2, but preferably a value within the range of 20 to 60, more preferably 40. The value of N may preferably be the number of frames for one walking cycle (for example, about 25 to 30 frames at about 30 fps), and more preferably the number of frames that can also cover one walking cycle of a subject with a walking disorder. (e.g., about 40 frames at about 30 fps). The value of N may be changed, for example, depending on the disease as a prediction object.

Figure 4A:
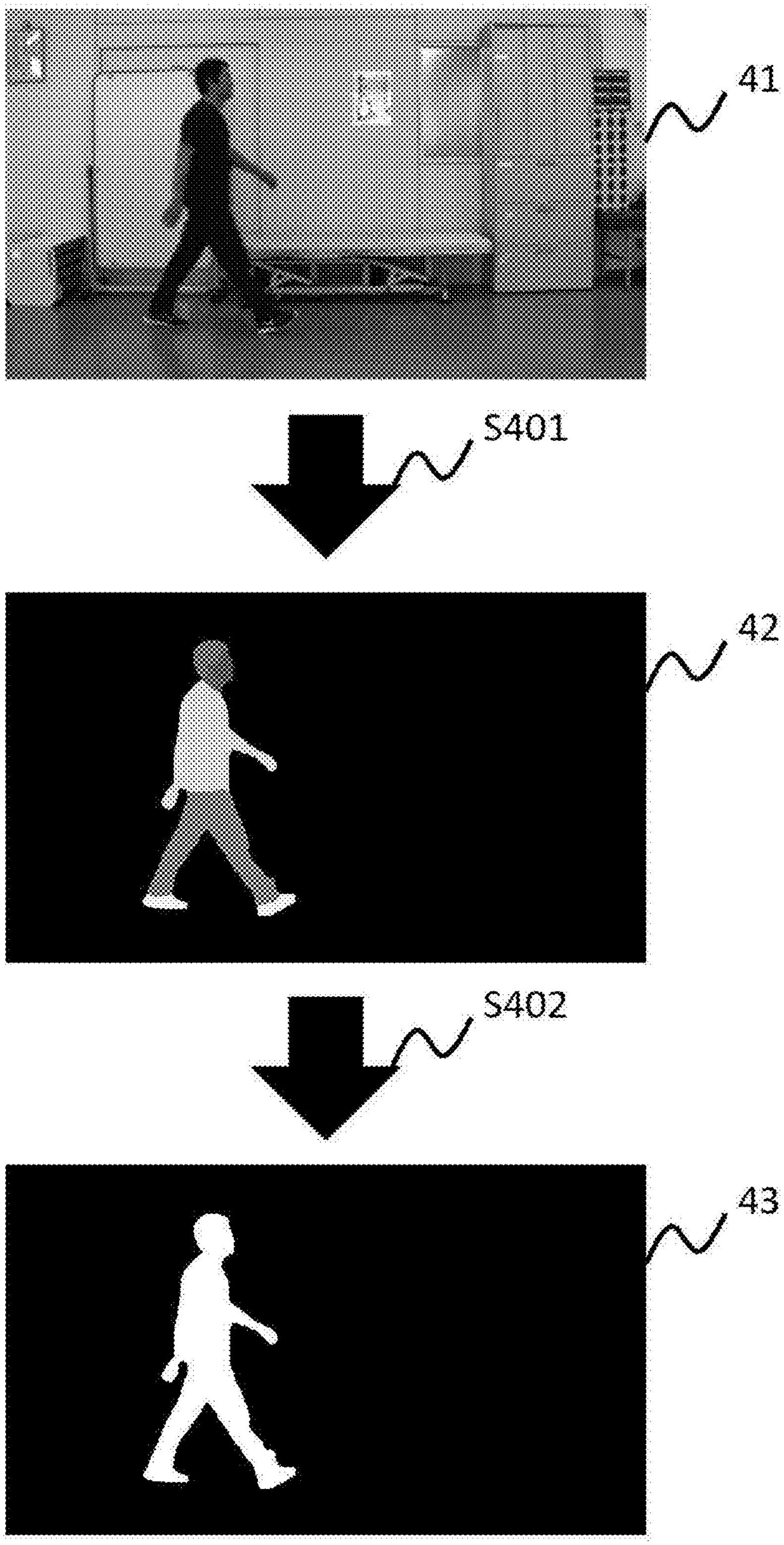
FIG. 4A is a diagram schematically illustrating an example of a flow of generating one silhouette image 43 from one image 41 by a generation means 122.

FIG. 4A schematically illustrates an example of a flow of generating one silhouette image 43 from one image 41 by the generation means 122.

First, the generation means 122 is provided with one image 41 from the receiving means 121.

In step S401, the generation means 122 generates a silhouette image 42 from the image 41. The silhouette image 42 is a multivalued image in which each part of the subject is represented by a different pixel value. In the example shown in FIG. 4A, in the silhouette image 42, the face, head, trunk, legs, and toes of the subject silhouette are each represented by different pixel values.

In step S402, the generation means 122 generates a silhouette image 43 from the silhouette image 42. The silhouette image 43 is a binary image in which the entire subject is represented by the same pixel value. The generation means 122 can generate the silhouette image 43 by expressing different pixel values of the silhouette of the subject in the silhouette image 42 with the same pixel value.

The generating unit 122 can generate a plurality of silhouette images from a plurality of images by performing such processing on each of the plurality of images. When a plurality of silhouette images are generated, for example, the flow shown in FIG. 4B may be performed.

In the above example, the silhouette image 43 which is a binary image is generated, but a silhouette image which is a multivalued image may be generated. In this case, step S402 may be omitted.

Figure 4B:
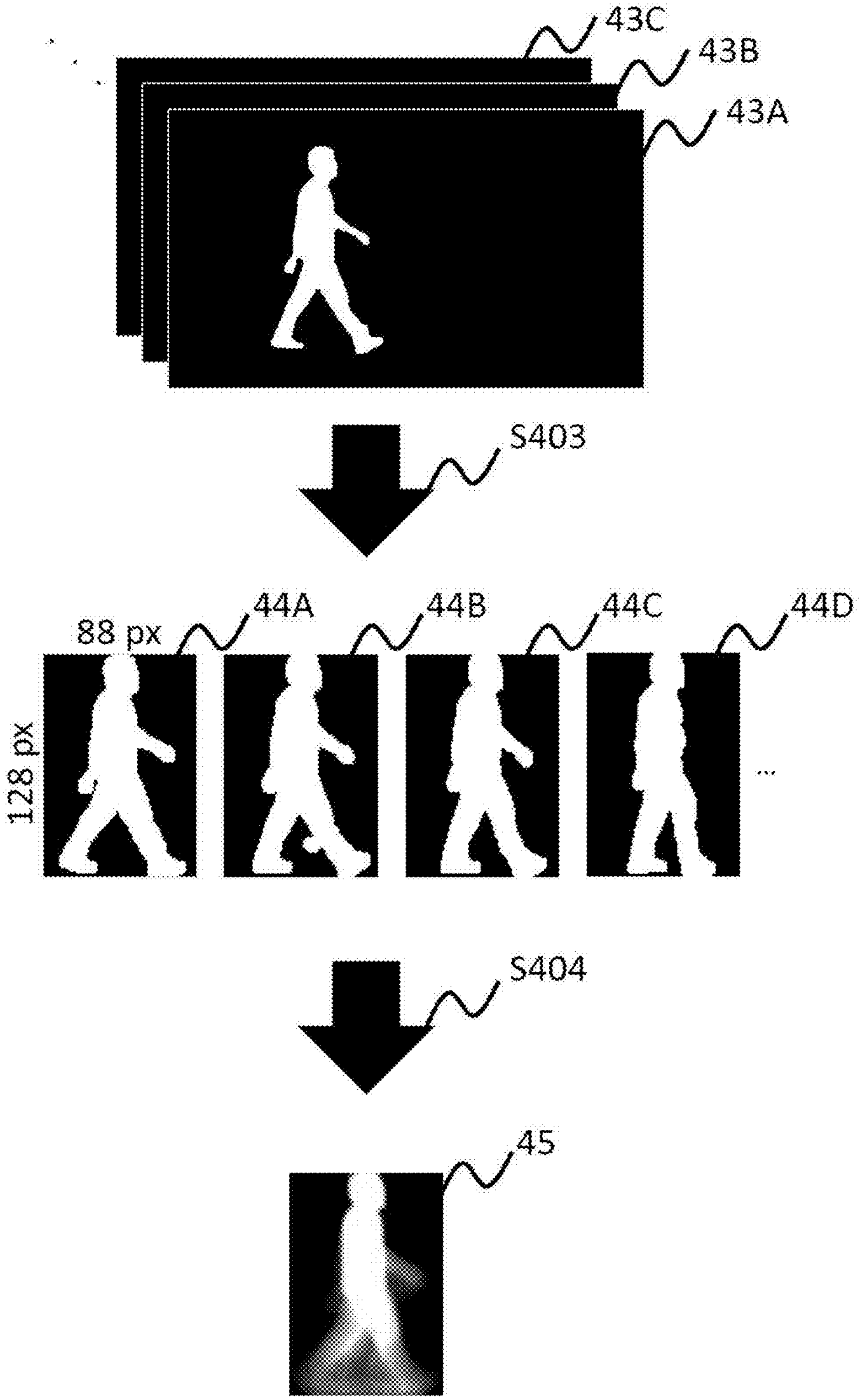
FIG. 4B is a diagram schematically illustrating an example of a flow of generating one silhouette image from a plurality of silhouette images 43A to 43C by a generation means 122.

FIG. 4B schematically illustrates an example of a flow in which the generation means 122 generates one silhouette image from the plurality of silhouette images 43A to 43C. Here, it is assumed that a plurality of silhouette images 43A, 43B, 43C, --- have been generated according to the flow shown in FIG. 4A.

In step S403, the generation means 122 generate a plurality of normalized silhouette regions 44A, 44B, 44C, by extracting a silhouette region of the subject from each of the plurality of silhouette images 43A, 43B, 43C, ---, and normalizing each of the plurality of extracted silhouette regions (i.e., sizes are made the same). In this example, normalization is performed using the height of the subject in the image as a reference. That is, each of the plurality of extracted silhouette regions is resized so that the height of the subject is the same in each of the plurality of silhouette regions extracted from each of the plurality of silhouette images 43A, 43B, 43C, ---, thereby, a plurality of normalized silhouette regions 44A, 44B, 44C, --- are generated. In this example, normalization is performed to give a silhouette region of 128 pixels length by 88 pixels wide.

In step S404, the generation means 122 generates one silhouette image 45 by averaging the plurality of normalized silhouette regions 44A, 44B, 44C, ---. The averaging can be performed by averaging the pixel values of each pixel for the plurality of normalized silhouette regions 44A, 44B, 44C, ---. For example, the pixel value $P_{ij}$ of the ij-th pixel of the silhouette image 45 can be calculated as follows:

$$P_{ij} = \frac{1}{n}\sum_{k=1}^{n} p_{ijk}. \quad \text{(Mathematical formula 1)}$$

Here, n is the number of the plurality of silhouette regions 44, $p_{ijk}$ is the pixel value of the ij-th pixel of the k-th silhouette region, and 0<i≤number of vertical pixels (in this example, 128), 0<j≤number of horizontal pixels (88 in this example).

In this way, the generation unit 122 can generate one silhouette image from a plurality of images through the processing shown in FIGS. 4A and 4B. The silhouette image generated by the generation means 122 is provided to the estimation means 123.

Referring again to FIG. 3A, the estimation means 123 is configured to estimate a condition related to at least one disease of the subject based on the at least one silhouette image.

For example, the estimation means 123 can estimate whether the subject has a certain disease or does not have a certain disease, as the condition of a certain disease. Alternatively, in addition to or in place of the above, the estimation means 123 can estimate the level of a certain disease that the subject has (for example, mild, moderate, or severe, or severity) as the condition of the certain disease. The severity can be expressed, for example, by the Japanese Orthopedic Association cervical spine score (cervical spine JOA score), which indicates the severity of cervical spondylosis myelopathy. Alternatively, in addition to or in place of the above, the estimation means 123 can estimate which of a plurality of diseases the subject has as the condition of a plurality of diseases.

Diseases whose conditions can be estimated by the estimation means 123 are typically diseases that cause a walking disorder, and may include, for example, locomotor diseases that cause a walking disorder, neuromuscular diseases that cause a walking disorder, cardiovascular disease that cause a walking disorder, and respiratory diseases that cause a walking disorder. More specifically, the disease includes, but not limited to, for example, cervical spondylotic myelopathy (CSM), lumbar canal stenosis (LCS), osteoarthritis (OA), neuropathy, intervertebral disc herniation, posterior longitudinal ligament bone OPLL, rheumatoid arthritis (RA), heart failure, hydrocephalus, peripheral artery disease (PAD), myositis, myopathy, Parkinson's disease, amyotrophic lateral sclerosis (ALS), spinocerebellar degeneration, multiple system atrophy, brain tumor, Lewy body dementia, subclinical fracture, drug addiction, meniscal injury, ligament injury, spinal cord infarction, myelitis, myelopathy, pyogenic spondylitis, discitis, bunion, chronic obstructive pulmonary disease (COPD), obesity, cerebral infarction, locomotive syndrome, frailty, and hereditary spastic paraplegia. In particular, the estimation means 123 can accurately estimate the condition of cervical spondylotic myelopathy (CSM), lumbar canal stenosis (LCS), osteoarthritis (OA), Parkinson's disease, rheumatoid arthritis (RA), and cerebral infarction. The estimation means 123 may also be configured to determine which organ the disease causing walking disorder relates to, and such determination may include determining whether it is a locomotor disease, a neuromuscular disease, a cardiovascular disease, or a respiratory disease.

The estimation means 123 can estimate a condition related to at least one disease of the subject using any algorithm. The estimation means 123 can estimate a condition related to at least one disease of the subject, for example, using a learned model. The learned model is a model that has learned the relationship between a learning silhouette image and a condition related to at least one disease of the object appearing in the learning silhouette image. The estimation means 123 can estimate, for example, a condition related to at least one disease of the subject on a rule basis based on the feature amount (for example, the contour shape of the subject when walking (e.g., the way the back bends, the way the legs bend, the way the arms swing, etc.)) acquired from at least one silhouette image.

The learned model may be any type of machine learning model. The machine learning model may be, for example, a neural network, more specifically a convolutional neural network. More specifically, an example of the machine learning model used is ResNet50 (https://arxiv.org/abs/1512.03385), but is not limited thereto.

In one example, the learned model may be a model created by processor section 140 described below or by processing 700 shown in FIG. 7A.

For example, since the learned model has learned the relationship between the learning silhouette image and the condition related to at least one disease of the object appearing in the learning silhouette image, if the silhouette image generated by the generating means 122 is input to the learned model, the learned model can output a condition related to at least one disease of the subject appearing in the silhouette image. The output can be, for example, one or both of a score indicating the presence of a particular disease and a score indicating the absence of the particular disease. Alternatively, the output may be, for example, a score indicating the level of a particular disease.

The results estimated by the estimation means 123 can be output to the outside of the computer system 100 via the interface section 110. For example, the estimated result may be transmitted to the subject's terminal device 300 via the interface section 110. Thereby, the subject can check its own condition via the own terminal device 300. At this time, the providing means that the computer system 100 may have may provide the subject with treatment or intervention according to the subject's condition, or may provide information corresponding to the subject's condition (for example, information that promotes behavior change, information supporting rehabilitation) to the subject. For example, the estimated result may be transmitted to the doctor's terminal device 300 via the interface section 110. This allows the doctor to utilize the estimated results in diagnosing the subject. At this time, for example, the providing means may provide the doctor with information according to the condition of the subject (e.g., information on recommended treatment or intervention, information on recommended rehabilitation). For example, the estimated result may be sent to the database section 200 via the interface section 110 and stored therein. Thereby, the estimated results can be referenced later or used later to update the learned model or to generate a new learned model.

In one embodiment, the estimation means 123 can estimate a health-related condition of the subject based on at least one silhouette image. The disease-related conditions described above are examples of health-related conditions. The health-related conditions may include, for example, conditions related to whole body health, conditions related to specific parts (e.g., lower limb conditions, upper limb conditions, internal organ conditions), and conditions related to specific functions (e.g., walking function condition, respiratory function condition). The health-related condition may be expressed as a binary value of good or bad, or may be expressed as a level or degree of health. The health-related condition may typically be the ability to walk. Walking ability can be expressed, for example, as walking age, which is a numerical value indicating the age level of the walking condition.

The estimation means 123 can estimate a health-related condition of the subject using any algorithm. For example, the estimation means 123 can estimate a health-related condition of the subject by using the learned model, as described above. The learned model is a model that has learned the relationship between a learning silhouette image and a health-related condition of the object appearing in the learning silhouette image. The estimation means 123 can estimate, for example, a health-related condition of the subject on a rule basis based on the feature amount (for example, the contour shape of the subject when walking (e.g., the way the back bends, the way the legs bend, the way the arms swing, etc.)) acquired from at least one silhouette image.

Figure 3B:
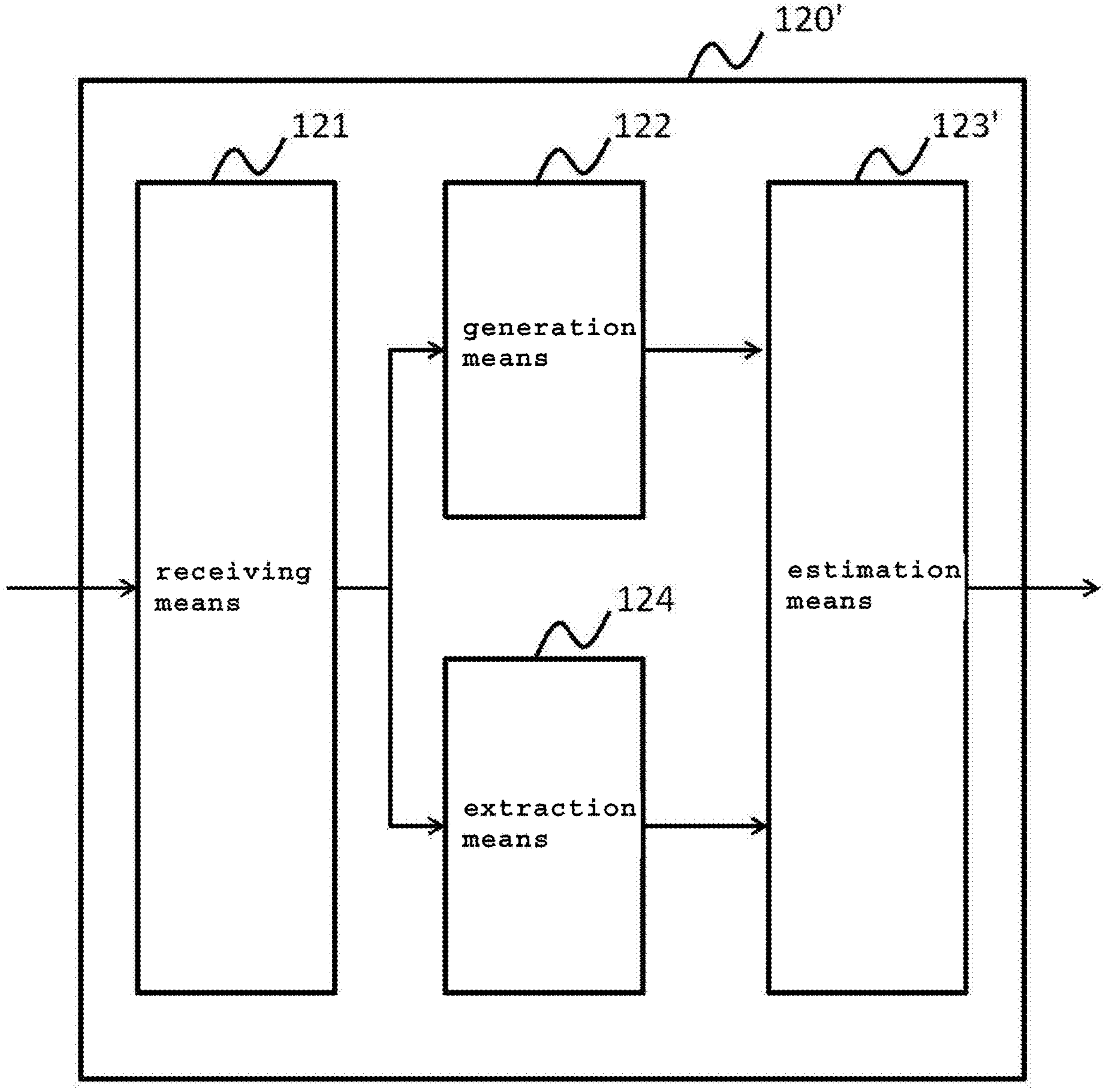
FIG. 3B is a diagram showing an example of the configuration of a processor section 120' in another embodiment.

FIG. 3B shows an example of the configuration of the processor section 120' in another embodiment.

The processor section 120' may have the same configuration as the processor section 120, except that it includes the extraction means 124. In FIG. 3B, components having the same configuration as those described above with reference to FIG. 3A are given the same reference numerals, and detailed description thereof will be omitted here.

The processor section 120' includes a receiving means 121, a generation means 122, an estimation means 123', and an extraction means 124.

The receiving means 121 is configured to receive a plurality of images photographed of the subject walking. The plurality of images received by the receiving means 121 are provided to the generation means 122 and the extraction means 124.

The generation means 122 is configured to generate a silhouette image of the subject from an image of the subject. The silhouette image generated by the generation means 122 is provided to the estimation means 123'.

The extraction means 124 is configured to extract the skeletal features of the subject from a plurality of images photographed of the subject. The extraction means 124 is configured, for example, to extract the skeletal features of the subject from the plurality of images received by the reception means 121. The extraction means 124 can generate time-series data of skeletal features by extracting skeletal features from each of the plurality of images. The extraction means 124 can extract the skeletal features using techniques known in the art. The extraction means 124 can extract the skeletal features using, for example, a method called Part Affinity Fields. A specific example of a skeleton extraction method using Part Affinity Fields includes, but is not limited to, a method using Openpose (https://arxiv.org/abs/1812.08008).

The extraction means 124 can represent a plurality of joints of the subject as points (keypoints) and extract skeletal features as a graph structure in which the points are connected. The graph structure can have any number of Keypoints.

Figure 5A:
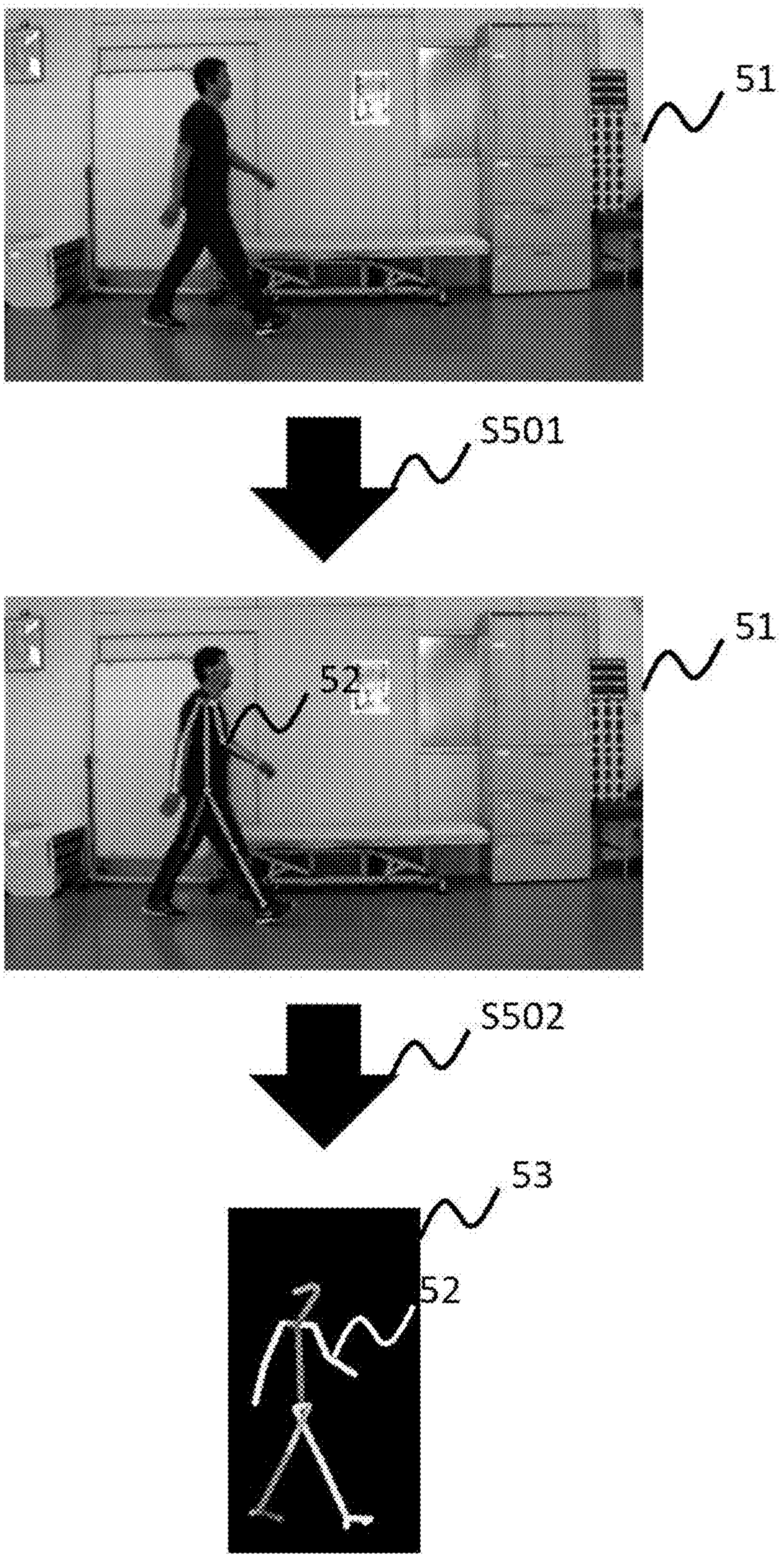
FIG. 5A is a diagram schematically illustrating an example of a flow of extracting a skeletal feature 52 from one image 51 by an extraction means 124.

FIG. 5A schematically illustrates an example of a flow in which the extraction means 124 extracts the skeletal features 52 from one image 51.

First, the extraction means 124 is provided with one image 51 from the receiving means 121.

In step S501, the extraction means 124 extracts the skeletal features 52 of the subject from the image 51. The skeletal features 52 are shown superimposed on the image 51. If this continues, the background information may become noise, so the background information may be removed.

In step S502, background information is removed and an image 53 having only skeletal features 52 is generated.

The generation unit 122 can generate a plurality of skeletal features (or a plurality of images having skeletal features) from a plurality of images by performing such processing on each of the plurality of images. The plurality of skeletal features (or the plurality of images having the skeletal features) are provided to the estimation means 123' as time-series skeletal feature data.

Referring again to FIG. 3B, the estimation means 123' can estimate at least one disease of the subject based on the silhouette image and the skeletal features.

The estimation means 123' can estimate, for example, whether the subject has a certain disease or does not have a certain disease, as the condition of a certain disease. Alternatively, in addition to or in place of the above, the estimation means 123' may estimate the level of a certain disease that the subject has (for example, mild, moderate, or severe, or severity) as the condition of the certain disease. The severity can be expressed, for example, by the Japanese Orthopedic Association cervical spine score (cervical spine JOA score), which indicates the severity of cervical spondylosis myelopathy.

Diseases whose conditions can be estimated by the estimation means 123' are typically diseases that cause a walking disorder, and may include, for example, locomotor diseases that cause a walking disorder, neuromuscular diseases that cause a walking disorder, cardiovascular disease that cause a walking disorder, and respiratory diseases that cause a walking disorder. More specifically, the disease includes, but not limited to, for example, cervical spondylotic myelopathy (CSM), lumbar canal stenosis (LCS), osteoarthritis (OA), neuropathy, intervertebral disc herniation, posterior longitudinal ligament bone (OPLL), rheumatoid arthritis (RA), heart failure, hydrocephalus, peripheral artery disease (PAD), myositis, myopathy, Parkinson's disease, amyotrophic lateral sclerosis (ALS), Spinocerebellar degeneration, multiple system atrophy, brain tumor, Lewy body dementia, subclinical fracture, drug addiction, meniscal injury, ligament injury, spinal cord infarction, myelitis, myelopathy, pyogenic spondylitis, discitis, bunion, chronic obstructive pulmonary disease (COPD), obesity, cerebral infarction, locomotive syndrome, frailty, and hereditary spastic paraplegia. Furthermore, the estimation means 123' may be configured to determine which organ the disease causing a walking disorder relates to, and such determination may include determining whether it is a locomotor disease, a neuromuscular disease, a cardiovascular disease, or a respiratory disease. In particular, the estimation means 123' can estimate the condition of lumbar canal stenosis (LCS), cervical spondylotic myelopathy (CSM) in the cervical region, ossification of posterior longitudinal ligament (OPLL) of the cervical spine, and intervertebral disc herniation, with high accuracy, based on the silhouette image and skeletal features.

For example, the estimation means 123' may be configured to estimate a condition related to at least one disease of the subject based on a result of estimating a condition related to at least one disease of the subject based on a silhouette image and a result of estimating a condition related to at least one disease of the subject based on a skeletal feature. The estimation means 123' may be, for example, made to obtain a first score indicating a condition related to at least one disease of the subject based on a silhouette image, obtain a second score indicating a condition related to at least one disease of the subject based on a skeletal feature, and estimate a condition related to at least one disease of the subject based on the first score and the second score. For example, when the first score indicates the presence or absence of a specific disease and the second score indicates the presence or absence of the specific disease, the estimation means 123' can determine whether a specific disease is present or not by comparing an added value of a first score indicating that a specific disease is present and a second score indicating that a specific disease is present with an added value of a second score indicating that there is no specific disease and a second score indicating that there is no specific disease. The first score and/or the second score may be converted into a value within the range of 0 to 1 by applying a predetermined function such as a softmax function or the like, and then added.

For example, if the first score obtained based on the skeletal feature is 3.0 for diseased and 2.0 for no disease, it becomes that 0.73 for diseased and 0.27 for no disease, by applying the softmax function. If the second score obtained based on the silhouette image is 0.45 for diseased and 0.55 for no disease, when the first score and second score are added, the added value leads to 0.73+0.45=1.18 for diseased and 0.27+0.55=0.82 for no disease. Since the score for disease present is greater, the subject's condition may be determined to be "diseased."

Note that when adding the first score and the second score, the first score and/or the second score may be weighted before being added. The degree of weighting may be, for example, a fixed value or a variable value. In the case of a variable value, the degree of weighting may be, for example, changed depending on the attributes of the subject, may be changed depending on the disease to be estimated, may be changed depending on the difference between the first score and the second score, or may be changed depending on any other arbitrary factor. The optimal degree of weighting may be determined by machine learning.

The score output from the estimation means 123' may have a correlation with, for example, an existing disease index, and can be converted into an existing disease index. As an example, the inventor of the present application found that a score output based on a silhouette image of a subject with cervical spondylosis myelopathy can be correlated with the cervical JOA score. This score was more pronounced in subjects with cervical JOA scores of 10 or higher. By using this correlation, it is also possible to express the output from the learned model by a cervical JOA score. By using a known index, it becomes easier to understand the meaning of the output from the estimation means 123'. For example, the receiving means 121 may receive images of subjects whose cervical JOA score is 10 or more, and may process only images of subjects whose cervical JOA score is 10 or more. Alternatively, images of subjects with a cervical JOA score of 10 or more may be extracted from the images received by the receiving means 121, and only images of subjects with a cervical JOA score of 10 or more may be processed.

When the estimation means 123' estimates a condition of a subject based on the result of estimating a condition related to at least one disease of the subject based on a silhouette image and the result of estimating a condition related to at least one disease of the subject based on a skeletal feature, the estimation means 123' can use a first learned model for estimation based on a silhouette image and a second learned model for estimation based on a skeletal feature.

The estimation means 123' can estimate a condition related to at least one disease of the subject, for example, using the first learned model. The first learned model is a model that has learned the relationship between a learning silhouette image and a condition related to at least one disease of the object appearing in the learning silhouette image.

The first learned model may be any type of machine learning model. A machine learning model may be, for example, a neural network, more specifically a convolutional neural network. More specifically, an example of the machine learning model used is ResNet50 (https://arxiv.org/abs/1512.03385), but is not limited thereto.

In one example, the first learned model may be a model created by processor section 140 or processor section 140', which will be described later, or by processing 700 or processing 710 shown in FIG. 7A or FIG. 7B.

For example, since the first learned model has learned the relationship between a learning silhouette image and a condition related to at least one disease of the object appearing in the learning silhouette image, when the silhouette image generated by the generating means 122 is input to the learned model, the learned model can output a condition related to at least one disease of the subject appearing in the silhouette image. The output can be, for example, one or both of a score indicating the presence of a particular disease and a score indicating the absence of the particular disease (e.g., the first score described above). Alternatively, the output may be, for example, a score indicating the level of a particular disease.

The estimation means 123' can estimate a condition related to at least one disease of the subject, for example, using the second learned model. The second learned model is a model that has learned the relationship between a learning skeletal feature and a condition related to at least one disease of the object from which the learning skeletal feature was acquired.

The second learned model may be any type of machine learning model. The machine learning model may be, for example, a neural network, more specifically a convolutional neural network. More specifically, examples of machine learning models used include, but not limited to, Spatial Temporal Graph Convolutional Network (ST-GCN), MS-G3D (https://arxiv.org/pdf/2003.14111.pdf), and the like.

In one example, the second learned model may be a model created by processor section 140' described below or by processing 710 shown in FIG. 7B.

For example, since the second learned model has learned the relationship between a learning skeletal feature and a condition related to at least one disease of the object for which the learning skeletal feature has been acquired, when the skeletal feature extracted by the extraction means 122 is input to the learned model, the learned model can output a condition related to at least one disease of the subject from which the skeletal feature has been extracted. The output can be, for example, one or both of a score indicating the presence of a particular disease and a score indicating the absence of the particular disease (e.g., the second score described above). Alternatively, the output may be, for example, a score indicating the level of a particular disease.

Note that in the above example, it has been explained that the silhouette image and the skeletal features are used independently to estimate a condition related to at least one disease of the subject, but the present disclosure is not limited to this, and it is also within the scope of the present disclosure to estimate a condition related to at least one disease of the subject by processing the silhouette images and the skeletal feature in relation to each other.

In one example, it is possible to estimate a condition related to at least one disease of the subject, using a learned model that has learned the relationship between a learning silhouette image, a learning skeletal feature, and a condition related to at least one disease of an object that appears in the learning silhouette image and from which the learning skeletal feature has been extracted. For example, when a silhouette image and a skeletal feature of a subject are input to such a learned model, the condition related to at least one disease of the subject can be estimated and output.

In another example, a silhouette image of a subject may be preprocessed based on a skeletal feature of the subject or a score obtained from the skeletal feature, and then the preprocessed silhouette image may be input to the learned model. The preprocessing can be any processing.

In another example, a skeletal feature of a subject may be preprocessed based on a silhouette image of the subject or a score obtained from the silhouette image, and then the preprocessed silhouette image may be input to the learned model. The preprocessing can be any processing.

The estimation means 123' can estimate a health-related condition of the subject through similar processing. The disease-related conditions described above are examples of health-related conditions. Conditions related to health may include, for example, conditions related to whole body health, conditions related to specific parts (e.g., condition of lower limbs, condition of upper extremities, condition of internal organs), and conditions related to specific functions (e.g., condition of walking function, condition of respiratory function). The health-related condition may be expressed as a binary value of good or bad, or may be expressed as a level or degree of health. A health-related condition may typically be walking ability, which may be expressed as walking age.

The result estimated by the estimation means 123' can be output to the outside of the computer system 100 via the interface section 110. For example, the estimated result may be transmitted to the subject's terminal device 300 via the interface section 110. This allows the subject to check the own condition via the own terminal device 300. For example, the estimated result may be transmitted to the doctor's terminal device 300 via the interface section 110. This allows the doctor to utilize the estimated results in diagnosing the subject. For example, the estimated result may be sent to the database section 200 via the interface section 110 and stored therein. Thereby, the estimated results can be referenced later or used later to update the learned model or to generate a new learned model.

Figure 3C:
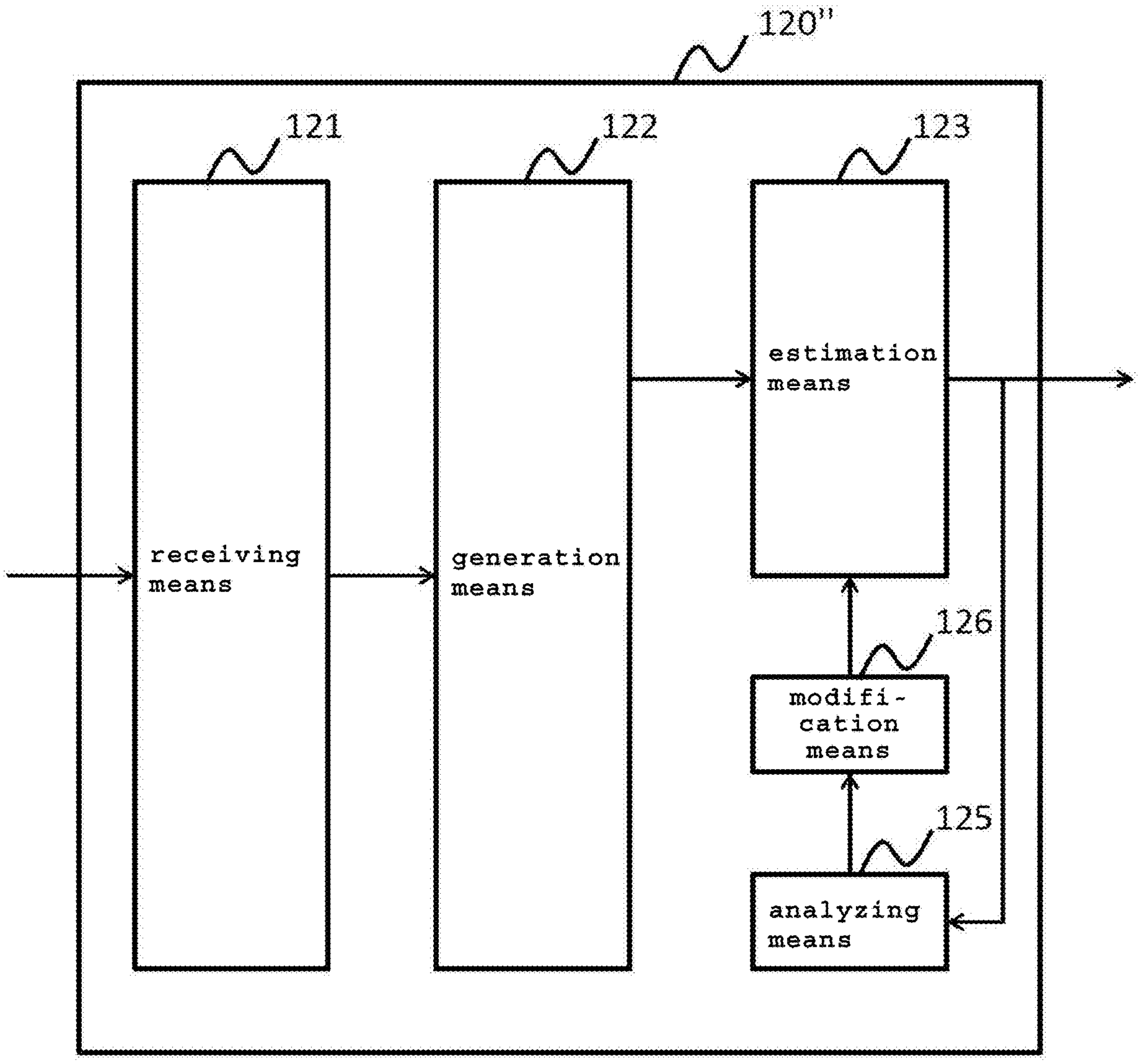
FIG. 3C is a diagram showing an example of the configuration of a processor section 120" in another embodiment.

FIG. 3C shows an example of the configuration of the processor section 120" in another embodiment.

The processor section 120" may have the same configuration as the processor section 120, except that it includes an analysis means 125 and a modification means 126. In FIG. 3C, components having the same configuration as those described above with reference to FIG. 3A are given the same reference numerals, and detailed description thereof will be omitted here. Note that the processor section 120" may have the same configuration as the processor section 120', except that the processor section 120" includes an analysis means 125 and a modification means 126.

The processor section 120" includes a receiving means 121, a generation means 122, an estimation means 123, an analyzing means 125, and a modification means 126.

The receiving means 121 is configured to receive a plurality of images photographed of the subject walking. The plurality of images received by the receiving means 121 are provided to the generation means 122 and the extraction means 124.

The generation means 122 is configured to generate a silhouette image of the subject from an image of the subject. The silhouette image generated by the generation means 122 is provided to the estimation means 123'.

The estimation means 123 is configured to estimate a condition related to at least one disease of the subject based on the at least one silhouette image. The estimation result by the estimation means 123 can be passed to the analysis means 125.

The analysis means 125 is configured to analyze the result of estimation by the estimation means 123. For example, the analysis means 125 can specify the basis for determining which area in the silhouette image generated by the generation means 122 the estimation means 123 focused on for performing estimation. In other words, it is possible to specify a region of interest that makes a relatively large contribution to the estimation result by the estimation means 123.

The analysis means 125 can identify the basis for the estimation using a method known in the technical field. The analysis means 125 can specify the basis for the estimation using, for example, an algorithm such as Grad-CAM, Grad-CAM++, Score-CAM, or the like. The analysis means 125 can preferably use Score-CAM to identify the basis for the estimation. Score-CAM is an algorithm that can visualize which areas in the image used for estimation were focused on for performing estimation, and this makes it possible to visually specify a region of interest that contributes relatively significantly to the estimation results. In Score-CAM, for example, differences in attention levels in estimation are output as a heat map.

It is possible that the accuracy of estimation by the estimation means 123 can be improved, by modifying the algorithm of the estimation means 123, so that a region with a high degree of attention (region of interest) contributes more to the estimation and/or a region with a low degree of attention does not contribute much to the estimation, based on the judgment basis specified by the analysis means 125. Additionally, it may be possible to focus on areas that are not usually focused on in the diagnosis performed by doctors, and an improvement in estimation accuracy can be expected.

The modification means 126 is configured to modify the algorithm of the estimation means 123 based on the judgment basis specified by the analysis means 125. For example, the modification means 126 can modify the algorithm of the estimation means 123 so that a region with a high degree of attention (region of interest) contributes more to the estimation, and/or a region with a low degree of attention contributes less to the estimation. For example, when the estimation means 123 uses a learned model, the modification means 126 can modify the learned model so that the region of interest contributes more to the estimation. For example, the modification unit 126 can modify the learned model by modifying the structure of the learned model, modifying the weighting of the learned model, or the like. For example, when the estimation means 123 performs rule-based estimation, the modification means 126 can modify the rule so that the region of interest contributes more to the estimation.

For example, when the processor section 120" has the same configuration as the processor section 120', the analysis means 125 can specify the basis for determining which part of the parts extracted by the extraction means the estimation means 123 focuses on for performing estimation. That is, it is possible to specify a region of interest (joint range of motion) that contributes relatively largely to the estimation result by the estimation means 123.

Figure 5B:
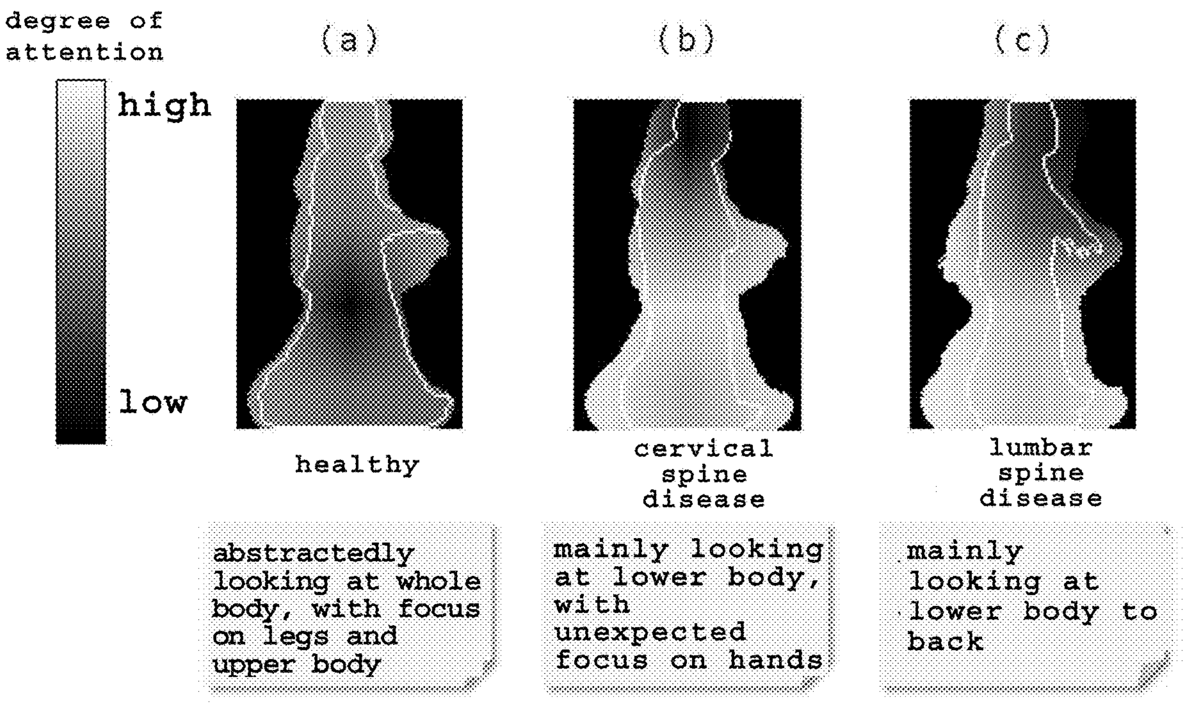
FIG. 5B is a diagram showing an example of the basis for judgment identified by an analysis means 125.

FIG. 5B shows an example of the basis for judgment identified by the analysis means 125. The degree of attention in estimation is shown in a heat map. In the heat map shown in FIG. 5B, the outline of the average silhouette image is shown superimposed on the heat map.

For example, when the analysis means 125 analyzes the result when the estimation means 123 estimates a condition related to at least one disease based on a silhouette image of a healthy person, a heat map as shown in FIG. 5B(a) is obtained. From this heat map, it can be seen that when the estimation means 123 performs estimation based on the silhouette image of a healthy person, it focuses on the whole body, focusing on the legs and upper body.

For example, when the analysis means 125 analyzes the result when the estimation means 123 estimates a condition related to at least one disease based on a silhouette image of a subject with a cervical spine disease, a heat map as shown in FIG. 5B(b) can be obtained. This heat map shows that when the estimation means 123 performs estimation based on a silhouette image of a subject with cervical spine disease, it focuses mainly on the lower body and also focuses on the hands.

For example, when the analysis means 125 analyzes the result when the estimation means 123 estimates a condition related to at least one disease based on a silhouette image of a subject with a lumbar spine disease, a heat map as shown in FIG. 5B(c) can be obtained. It can be seen from this heat map that when the estimation means 123 performs estimation based on a silhouette image of a subject with lumbar spine disease, it focuses mainly on from the lower body to back.

By modifying the algorithm of the estimation means 123 based on these results, it is expected that the accuracy of the estimation means 123 will be improved. For example, when estimating the presence or absence of cervical spine disease, the accuracy of the estimation means 123 can be expected to improve by modifying the algorithm to focus on the lower body and also on the hands. For example, when estimating the presence or absence of cervical spine disease, the accuracy of the estimation means 123 can be expected to improve by modifying the algorithm to focus on from the lower body to back.

The estimation means 123 can perform estimation using a modified algorithm. The results estimated by the estimation means 123 can be output to the outside of the computer system 100 via the interface section 110.

The computer system 100 may include a processor section 140 or a processor section 140' in addition to or in place of the processor section 120, processor section 120', or processor section 120" described above. The processor section 140 or processor section 140' can perform processing for creating a learned model used in the estimation means 123 or 123' described above. When the computer system 100 includes a processor section 140 or a processor section 140' in addition to the processor section 120 or a processor section 120' described above, the processor section 140 or a processor section 140' may be implemented as the same component as the processor section 120 or the processor section 120' or the processor section 120", or may be implemented as a separate component.

Figure 3D:
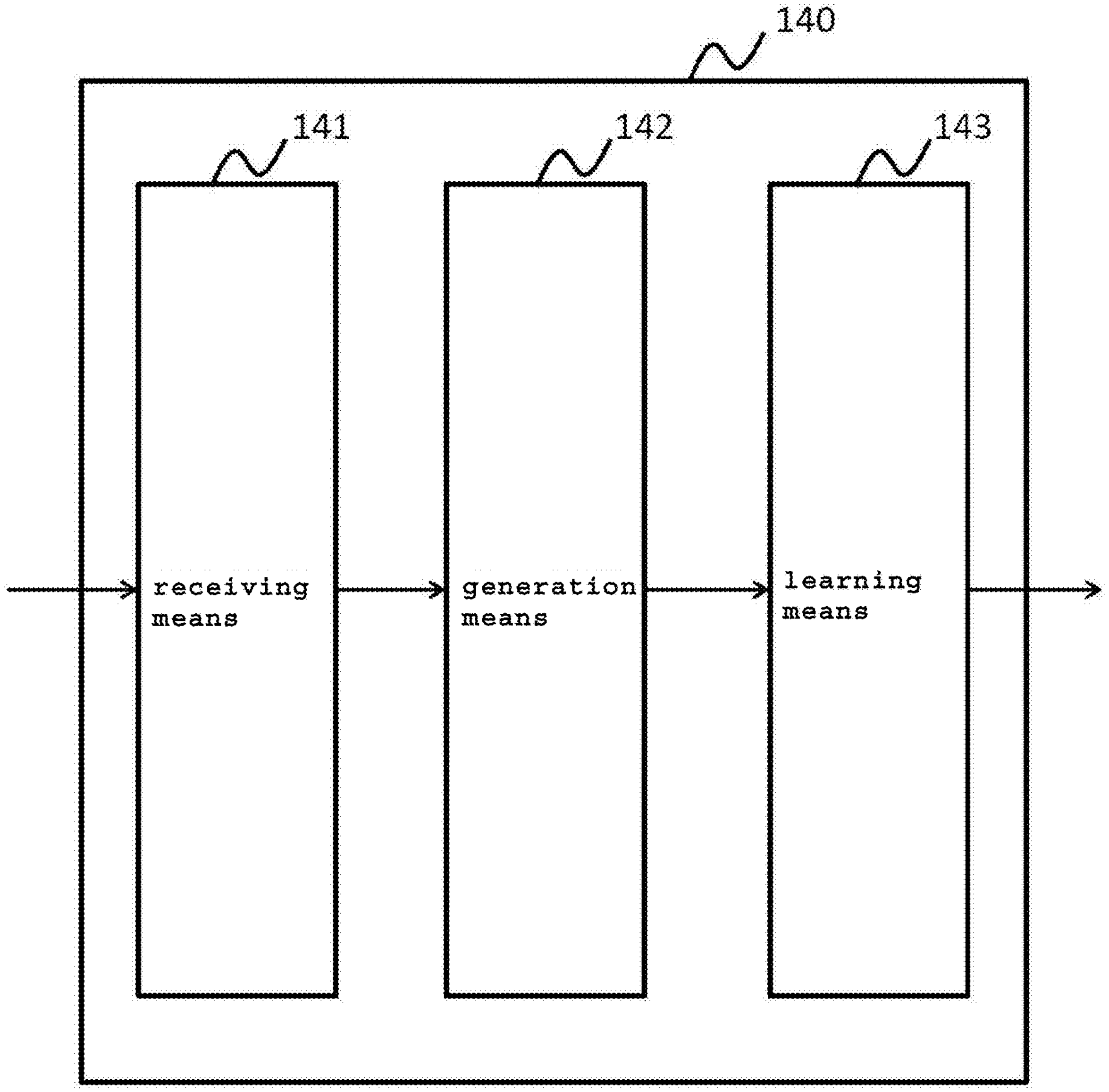
FIG. 3D is a diagram showing an example of the configuration of a processor section 140 in one embodiment.

FIG. 3D shows an example of the configuration of the processor section 140 in one embodiment.

The processor section 140 includes a receiving means 141, a generation means 142, and a learning means 143.

The receiving means 141 is configured to receive, for each of the plurality of objects, a plurality of images photographed of the object walking. The receiving means 141 can receive a plurality of images from outside the computer system 100 via the interface section 110. The plurality of images for each object among the plurality of objects may be, for example, those transmitted from the terminal device of each object to the computer system 100, or those stored in the database section 200, transmitted from the database section 200 to the computer system 100.

The plurality of images may be, for example, a plurality of images photographed by continuously photographing still images, or a plurality of frames forming a video. The plurality of images may have any frame rate, but preferably the frame rate may be between 20 fps and 60 fps, more preferably 30 fps.

The receiving means 141 can further receive information indicating a condition related to at least one disease for each of the plurality of objects.

The plurality of images received by the receiving means 141 are provided to the generation means 142. The information indicating a condition related to at least one disease received by the receiving means 141 is provided to the learning means 143.

The generation means 142 is configured to generate a silhouette image of an object from an image of the object. It has the same configuration as the generation means 122 and can perform the same processing. Description thereof will be omitted here.

The silhouette image generated by the generation means 142 is provided to the learning means 143.

The learning means 143 is configured to cause a machine learning model to learn by using at least one silhouette image of the object as input training data and using at least one disease-related condition of the object as output training data. The output training data may be a value indicating the presence or absence of a disease or a score indicating the degree of the disease. The value indicating the presence or absence of a disease may be, for example, a one-dimensional value (e.g., 0 meaning absence of disease, 1 meaning presence of disease), a two-dimensional value (e.g., (1,0) meaning absence of disease, (0,1) meaning presence of disease, (1,1) meaning presence of first disease and presence of second disease, (0,0) meaning absence of first disease and absence of second disease, etc.), or may be a three or more-dimensional value.

In one example, the set of the input training data and the output training data can be (at least one silhouette image of the first object, a value indicating the presence or absence of a specific disease in the first object), (at least one silhouette image of the second object, a value indicating the presence or absence of a specific disease in the second object), ---- (at least one silhouette image of the n-th object, a value indicating the presence or absence of a specific disease in the n-th object). When a silhouette image is input, the learned model learned using such a set can output a value indicating the presence or absence of a specific disease in a subject appearing in the silhouette image.

In another example, the set of the input training data and the output training data can be (at least one silhouette image of the first object, a value indicating the presence or absence of a specific disease in the first object), (at least one silhouette image of the second object, a value indicating the presence or absence of a specific disease in the second object), ---- (at least one silhouette image of the n-th object, a value indicating the presence or absence of a specific disease in the n-th object). When a silhouette image is input, the learned model learned using such a set can output a score indicating the degree of a specific disease of a subject appearing in the silhouette image.

The learned model created in this way can be used by the processor section 120 or processor section 120'. Further, the parameters of the learned model created in this way can be stored in the database section 200 or other storage medium.

Figure 3E:
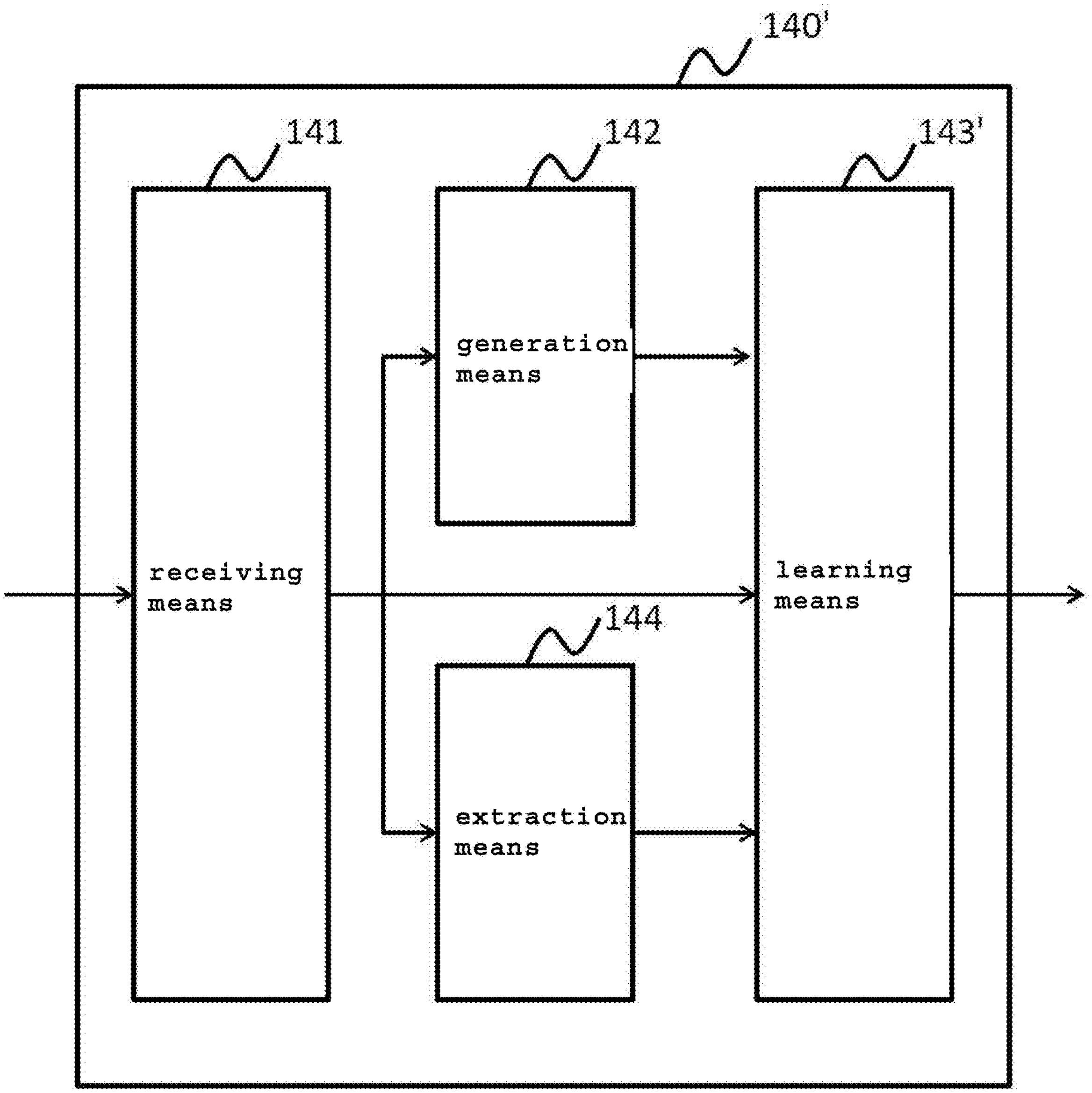
FIG. 3E is a diagram showing an example of the configuration of a processor section 140' in another embodiment.

FIG. 3E shows an example of the configuration of the processor section 140' in another embodiment.

The processor section 140' may have the same configuration as the processor section 140, except that it includes an extraction means 144. In FIG. 3E, components having the same configuration as those described above with reference to FIG. 3D are given the same reference numerals, and detailed description of each component will be omitted.

The processor section 140' includes a receiving means 141, a generation means 142, a learning means 143', and an extraction means 144.

The receiving means 141 is configured to receive, for each of the plurality of objects, a plurality of images photographed of the object walking. Moreover, the receiving means 141 can further receive information indicating a condition related to at least one disease for each of the plurality of objects. The plurality of images received by the receiving means 141 are provided to the generation means 142 and the extraction means 144. Information indicating a condition related to at least one disease is provided to the learning means 143'.

The generation means 142 is configured to generate a silhouette image of the object from an image of the object. The silhouette image generated by the generation means 142 is provided to the learning means 143'.

The extraction means 144 is configured to extract a skeletal feature of the object from a plurality of images in which the object is photographed. The extraction means 144 has the same configuration as the extraction means 124 and can perform the same processing. Description thereof will be omitted here. The skeletal feature extracted by the extraction means 144 is provided to the learning means 143'.

The learning means 143 is configured to cause a machine learning model to learn at least one silhouette image and a skeletal feature of the object. For example, the learning means 143 can be made to cause a first machine learning model to learn at least one silhouette image of the object as input training data and a condition related to at least one disease of the object as output training data, and cause a second machine learning model to learn a skeletal feature of the object as input training data and a condition related to at least one disease of the object as output training data. Alternatively, for example, the learning means 143 can cause a machine learning model to learn at least one silhouette image and skeletal feature of the object as input training data, and a condition related to at least one disease of the object as output training data.

The output training data may be a value indicating the presence or absence of a disease or a score indicating the degree of the disease. The value indicating the presence or absence of a disease may be, for example, a one-dimensional value (e.g., 0 meaning absence of disease, 1 meaning presence of disease), a two-dimensional value (e.g., (1,0) meaning absence of disease, (0,1) meaning presence of disease, (1,1) meaning presence of first disease and presence of second disease, (0,0) meaning absence of first disease and absence of second disease, etc.), or may be a three or more-dimensional value.

For example, when a first machine learning model is caused to learn at least one silhouette image of the object as input training data and a condition related to at least one disease of the object as output training data, the pair of the input training data and the output training data can be (at least one silhouette image of the first object, a value indicating the presence or absence of a specific disease in the first object), (at least one silhouette image of the second object, a value indicating the presence or absence of a specific disease in the second object), ---- (at least one silhouette image of the n-th object, a value indicating the presence or absence of a specific disease in the n-th object). When a silhouette image is input, the first learned model learned using such a set can output a value indicating the presence or absence of a specific disease in a subject appearing in the silhouette image.

In another example, the set of the input training data and the output training data can be (at least one silhouette image of the first object, a score indicating the degree of a specific disease of the first object), (at least one silhouette image of the second object, a score indicating the degree of a specific disease of the second object), ---- (at least one silhouette image of the n-th object, a score indicating the degree of a specific disease of the n-th object). When a silhouette image is input, the first learned model learned using such a set can output a score indicating the degree of a specific disease of a subject appearing in the silhouette image.

In another example, the set of the input training data and the output training data can be (at least one silhouette image of the first object, (a value indicating the presence or absence of the first disease in the first object, a value indicating the presence or absence of the second disease in the object, ---- a value indicating the presence or absence of the m-th disease in the first object)), (at least one silhouette image of the second object, (a value indicating the presence or absence of the first disease in the second object, a value indicating the presence or absence of the second disease in the second object, ---- a value indicating the presence or absence of the m-th disease in the second object)), ----- (at least one silhouette image of the n-th object, (a value indicating the presence or absence of the first disease in the n-th object, a value indicating the presence or absence of the second disease in the n-th object, ---- a value indicating the presence or absence of the m-th disease in the n-th object)). When a silhouette image is input, the first learned model learned using such a set can output each of a value indicating the presence or absence of the first disease, a value indicating the presence or absence of the second disease, a --- value indicating the presence or absence of the m-th disease, of the subject appearing in the silhouette image. Thereby, it is possible to estimate which disease among a plurality of diseases the subject has. This can be useful in determining which organ the disease that cause a walking disorder is related to, for example, this helps determine whether the disease which the subject may have is a locomotor disease, a neuromuscular disease, a cardiovascular disease, or a respiratory disease, and for example, it can be useful in determining which department the subject should first visit.

For example, when a second machine learning model is caused to learn a skeletal feature of the object as input training data and a condition related to at least one disease of the object as output training data, the pair of the input training data and the output training data can be (a skeletal feature of the first object, a value indicating the presence or absence of a specific disease in the first object), (a skeletal feature of the second object, a value indicating the presence or absence of a specific disease in the second object), ---- (a skeletal feature of the n-th object, a value indicating the presence or absence of a specific disease in the n-th object). When a skeletal feature is input, the second learned model learned using such a set can output a value indicating the presence or absence of a specific disease in the subject from whom the skeletal feature has been acquired.

In another example, the set of the input training data and the output training data can be (a skeletal feature of the first object, a score indicating the degree of a specific disease of the first object), (a skeletal feature of the second object, a score indicating the degree of a specific disease of the second object), ---- (a skeletal feature of the n-th object, a score indicating the degree of a specific disease of the n-th object). When a skeletal feature is input, the second learned model learned using such a set can output a score indicating the degree of a specific disease of the subject from whom the skeletal feature has been acquired.

In another example, the set of the input training data and the output training data can be (a skeletal feature of the first object, (a value indicating the presence or absence of the first disease in the first object, a value indicating the presence or absence of the second disease in the first object, --- a value indicating the presence or absence of the m-th disease in the first object)), (a skeletal feature of the second object, (a value indicating the presence or absence of the first disease in the second object, a value indicating the presence or absence of the second disease in the second object, --- a value indicating the presence or absence of the m-th disease in the second object), ---- (a skeletal feature of the n-th object, (a value indicating the presence or absence of the first disease in the n-th object, a value indicating the presence or absence of the second disease in the n-th object, --- a value indicating the presence or absence of the m-th disease in the n-th object)). When a skeletal feature is input, the second learned model learned using such a set can output each of a value indicating the presence or absence of the first disease, a value indicating the presence or absence of the second disease, --- a value indicating the presence or absence of the m-th disease, of the subject from whom its skeletal feature has been acquired. Thereby, it is possible to estimate which disease among a plurality of diseases the subject has. This can be useful in determining which organ the disease that cause a walking disorder is related to, for example, this helps determine whether the disease which the subject may have is a locomotor disease, a neuromuscular disease, a cardiovascular disease, or a respiratory disease, and for example, it can be useful in determining which department the subject should first visit.

For example, when a machine learning model is caused to learn at least one silhouette image and a skeletal feature of the object as input training data and a condition related to at least one disease of the object as output training data, the pair of the input training data and the output training data can be (at least one silhouette image and a skeletal feature of the first object, a value indicating the presence or absence of a specific disease in the first object), (at least one silhouette image and a skeletal feature of the second object, a value indicating the presence or absence of a specific disease in the second object), ---- (at least one silhouette image and a skeletal feature of the n-th object, a value indicating the presence or absence of a specific disease in the n-th object). When a silhouette image and a skeletal feature are input, the learned model learned using such a set can output a value indicating the presence or absence of a specific disease in the subject who appears in the silhouette image and whose skeletal feature has been acquired.

In another example, the set of the input training data and the output training data can be (at least one silhouette image and a skeletal feature of the first object, a score indicating the degree of a specific disease of the first object), (at least one silhouette image and a skeletal feature of the second object, a score indicating the degree of a specific disease of the second object), --- (at least one silhouette image and a skeletal feature of the n-th object, a score indicating the degree of a specific disease of the n-th object). When a silhouette image and a skeletal feature are input, the learned model learned using such a set can output a score indicating the degree of a specific disease of the subject who appears in the silhouette image and whose skeletal feature has been acquired.

In another example, the set of the input training data and the output training data can be (at least one silhouette image and a skeletal feature of the first object, (a value indicating the presence or absence of the first disease in the first object, a value indicating the presence or absence of the second disease in the first object, --- a value indicating the presence or absence of the m-th disease in the first object)), (at least one silhouette image and a skeletal feature of the second object, (a value indicating the presence or absence of the first disease in the second object, a value indicating the presence or absence of the second disease in the second object, --- a value indicating the presence or absence of the m-th disease in the second object)), --- (at least one silhouette image and a skeletal feature of the n-th object, (a value indicating the presence or absence of the first disease in the n-th object, a value indicating the presence or absence of the second disease in the n-th object, --- a value indicating the presence or absence of the m-th disease in the n-th object)). When a silhouette image and a skeletal feature are input, the learned model learned using such a set can output each of a value indicating the presence or absence of the first disease, a value indicating the presence or absence of the second disease, --- a value indicating the presence or absence of the m-th disease, of the subject who appears in the silhouette image and whose skeletal feature has been acquired. Thereby, it is possible to estimate which disease among a plurality of diseases the subject has. This can be useful in determining which organ the disease that causes a walking disorder is related to, for example, this helps determine whether the disease which the subject may have is a locomotor disease, a neuromuscular disease, a cardiovascular disease, or a respiratory disease, and for example, it can be useful in determining which department the subject should first visit.

The learned model created in this way can be used by the processor section 120'. Further, the parameters of the learned model created in this way can be stored in the database section 200.

Note that each component of the computer system 100 described above may be composed of a single hardware component or may be composed of a plurality of hardware components. When configured with a plurality of hardware components, it does not matter how each hardware component is connected. Each hardware component may be connected wirelessly or by wire. The computer system 100 of the present invention is not limited to any particular hardware configuration. It is also within the scope of the present invention that the processor sections 120, 120', 140, 140' be configured by analog circuits instead of digital circuits. The configuration of the computer system 100 of the present invention is not limited to that described above as long as its functions can be realized.

3. Processing by Computer System for Estimating Condition of Subject

Figure 6A:
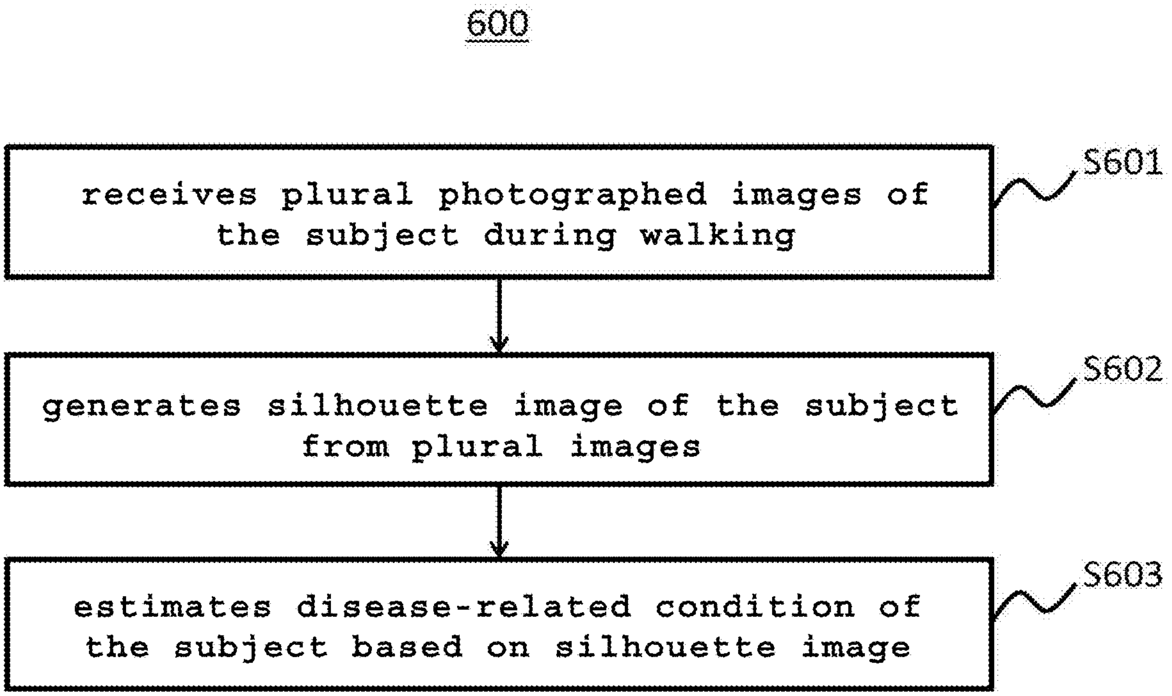
FIG. 6A is a flowchart showing an example of processing (processing 600) by a computer system 100 for estimating a condition of a subject.

FIG. 6A is a flowchart illustrating an example of processing (processing 600) by the computer system 100 for estimating the condition of the subject. The processing 600 is executed by a processor section 120 of the computer system 100. The processing 600 is processing for estimating a condition of a subject based on a silhouette image generated from a plurality of images photographed of the subject walking. The condition of a subject may be a health-related condition, and the health-related condition includes at least one disease-related condition. In the following, estimating a disease-related condition will be explained as an example, but it is understood that the following processing can be similarly applied to estimate other health-related conditions (e.g., estimating walking ability, estimating health level). In the present specification, the disease-related condition includes also a condition in which the object does not actually suffer from the disease (also referred to as "presymptomatic"), and in one embodiment, the disease-related condition may include only conditions in which the object actually suffers from the disease. Therefore, the health-related condition includes a disease-related condition and a condition other than a disease-related condition, and may include either or both of them.

In step S601, the receiving means 121 of the processor section 120 receives a plurality of images photographed of the subject walking. The plurality of images received by the receiving means 121 are provided to the generation means 122.

In step S602, the generation means 122 of the processor section 120 generates at least one silhouette image of the subject from the plurality of images received in step S601. The generation means 122 can generate the silhouette image using techniques known in the technical field. The generation means 122 can generate a plurality of silhouette images from a plurality of images, and preferably can generate one silhouette image from a plurality of images.

The generation means 122 can generate at least one silhouette image by, for example, extracting a plurality of silhouette regions from a plurality of images, normalizing the extracted plurality of silhouette regions, and averaging the plurality of normalized silhouette regions. By averaging a plurality of silhouette images, the amount of data can be reduced without significantly impairing the information amount of the silhouette images used.

In step S603, the estimation means 123 of the processor section 120 estimates the subject's disease-related condition based on at least one silhouette image generated in step S602. The estimation means 123 can estimate a condition related to at least one disease of the subject, for example, using a learned model. The learned model may be a model created by processor section 140 or by processing 700 shown in FIG. 7A.

The results estimated by the processing 600 can be output to the outside of the computer system 100 via the interface section 110. For example, the estimated result may be transmitted to the subject's terminal device 300 via the interface section 110. This allows the subject to check the own condition via the own terminal device 300. At this time, for example, treatment or intervention depending on the subject's condition may be provided to the subject, or information appropriate to the subject's condition (for example, information to encourage behavior change, information to support rehabilitation) may be provided to the subject. For example, the estimated result may be transmitted to the doctor's terminal device 300 via the interface section 110. This allows the doctor to utilize the estimated results in diagnosing the subject. At this time, for example, information depending on the condition of the subject (for example, information on recommended treatment or intervention, information on recommended rehabilitation) may be provided to the doctor. For example, the estimated result may be sent to the database section 200 via the interface section 110 and stored therein. Thereby, the estimated results can be referenced later or used later to update the learned model or to generate a new learned model.

(Companion Medical Care)

In one aspect, the present disclosure provides a method of treating, preventing, or improving a health condition, disorder, or disease of a subject by estimating a condition of health condition, disorder, or disease of the subject. In one aspect, the present disclosure provides a method for treating, preventing, or improving a health condition, disorder, or disease in a subject, the method comprising: (A) receiving a plurality of images photographed of the subject walking, (B) generating at least one silhouette image of the subject from the plurality of images, (C) estimating a health-related condition of the subject at least based on the at least one silhouette image, (D) calculating a method for treatment, prevention, or improvement to be applied to the subject based on the health-related condition of the subject, (E) administering the method for treatment, prevention, or improvement to the subject, and (F) repeating the steps (A) to (E) as necessary.

Such methods for prevention or improvement may be performed at existing medical facilities such as clinics, may be achieved through home medical care, or may be performed through telemedicine, and in the case of a presymptomatic condition, this may be done, for example, at a sports gym, shopping center, etc., or may be implemented on a mobile terminal or a wearable device such as a smartphone application.

In the present specification, methods for treatment, intervention, prevention, or amelioration can include, for example, at least one of the following:

[Conservative Treatment]

[Medication Medical Care]

[Patient education and lifestyle guidance: for example, guidance on self-management programs including exercise, dietary guidance, exercise guidance, patient education in the form of lectures or discussions, exercise classes, knee diary (whether to exercise or not, degree of pain), lifestyle Guidance]

[Weight loss therapy]

[Exercise therapy: e.g., muscle-strengthening exercise (isokinetic muscle-strengthening exercise, static stretch+isokinetic exercise, proprioceptive neuromuscular facilitation (PNF) stretch+isokinetic exercise), aerobic exercise, stretching, and Joint range of motion exercise, coordination exercise (foot dexterity improvement training, balance exercise, kinesthetic training using a sling suspension, computer-based foot dexterity improvement training (target-matching foot-stepping exercise)), vibration stimulation therapy (vibration exercise)]

[Manual therapy (Macquaire injury management group knee protocol)]

[Plantar disc therapy]

[Orthotic therapy]

[Taping: for example, taping related to pain, taping related to functional impairment]

[Physical therapy: for example, ultrasound therapy, spa therapy, TENS therapy (transcutaneous electrical nerve stimulation: TENS), functional electrical stimulation (FES), hydrotherapy, hot pack, biomagnetic therapy, shortwave diathermy, interferential current therapy, pulsed electrical stimulator, noninvasive interactive neurostimulation, periosteal stimulation therapy, laser therapy, combined use of physical therapy and exercise therapy] [Physical therapy intervention after open treatment]

[Total knee arthroplasty (TKA): e.g., continue passive movement (CPM) devices, range of motion exercises and slider board exercises, progressive muscle strengthening exercises, functional exercise therapy and balance exercises, vibration stimulation exercise therapy, improving muscle activity through transcutaneous electrical stimulation, preoperative physical therapy and patient education, preoperative physical therapy and patient education]

[High tibial osteotomy (HTO), unicompartmental knee arthroplasty (UKA)]

The processing 600 may be executed by the processor section 120", in which case the results estimated by the processing 600 are used to be analyzed by the analysis means 125. Based on the analysis, the algorithm of the estimation means 123 can be modified by the modification means 126. The processing 600 can be repeated using the modified algorithm.

Figure 6B:
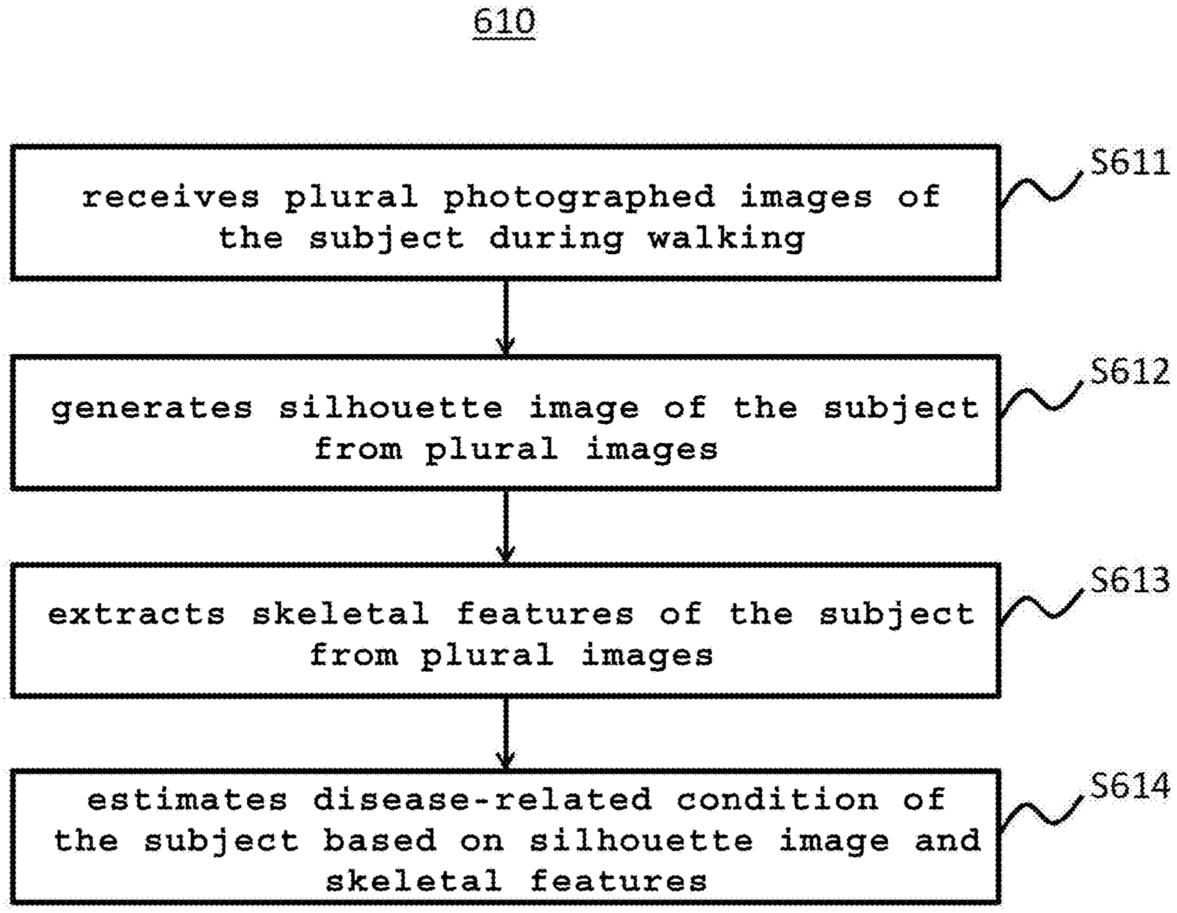
FIG. 6B is a flowchart showing another example of processing (processing 610) by a computer system 100 for estimating a condition of a subject.

FIG. 6B is a flowchart showing another example of the processing (processing 610) by the computer system 100 for estimating a condition of a subject. The processing 610 is executed by processor section 120' of computer system 100. The processing 610 is processing for estimating a condition of a subject based on a silhouette image generated from a plurality of images photographed of the subject walking and a skeletal feature extracted from the plurality of images. The condition of the subject may be a health-related condition, and the health-related condition includes at least one disease-related condition. In the following, estimating a disease-related condition will be explained as an example, but it is understood that the following processing can be similarly applied to estimate other health-related conditions (e.g., estimating walking ability, estimating health level).

In step S611, the receiving means 121 of the processor section 120' receives a plurality of images photographed of the subject walking. Step S611 is similar to step S601. The plurality of images received by the receiving means 121 are provided to the generation means 122.

In step S612, the generation means 122 of the processor section 120' generates at least one silhouette image of the subject from the plurality of images received in step S611. Step S612 is similar to step S602.

In step S613, the extraction means 124 of the processor section 120' extracts a skeletal feature of the subject from the plurality of images received in step S611. The extraction means 124 can generate a silhouette image using techniques known in the art. The extraction means 124 can generate time-series data of the skeletal feature by extracting skeletal features from each of the plurality of images.

In step S614, the estimation means 123' of the processor section 120' estimates the disease-related condition of the subject based on the at least one silhouette image generated in step S612 and the skeletal features extracted in step S613. The estimation means 123' can estimate a condition related to at least one disease of the subject, for example, using the learned model. The learned model may be a model created by processor section 140 or processor section 140' or by processing 710 shown in FIG. 7A or 7B.

For example, the estimation means 123' can be configured to estimate a condition related to at least one disease of the subject based on a result of estimating a condition related to at least one disease of a subject based on a silhouette image, and a result of estimating a condition related to at least one disease of a subject based on a skeletal feature. The estimation means 123' can be configured to, for example, obtain a first score indicating a condition related to at least one disease of the subject based on a silhouette image, obtain a second score indicating a condition related to at least one disease of the subject based on a skeletal feature, and estimate a condition related to at least one disease of the subject based on the first score and the second score. For example, when the first score indicates the presence or absence of a specific disease and the second score indicates the presence or absence of the specific disease, the estimation means 123' can determine whether a specific disease is present or not by comparing an added value of a first score indicating that a specific disease is present and a second score indicating that a specific disease is present with an added value of a second score indicating that there is no specific disease and a second score indicating that there is no specific disease. The first score and/or the second score may be converted into a value within the range of 0 to 1 by applying a predetermined function such as a softmax function, and then added. The score output from the estimation means 123' can be converted into an existing disease index based on correlation with the existing disease index, for example. For example, the score output from the estimation means 123' can be converted into a cervical JOA score.

The results estimated by the processing 610 can be output to the outside of the computer system 100 via the interface section 110. For example, the estimated result may be transmitted to the subject's terminal device 300 via the interface section 110. This allows the subject to check the own condition via the own terminal device 300. At this time, similar to processing 600, for example, treatment or intervention depending on the subject's condition may be provided to the subject, or information depending on the subject's condition (for example, information to encourage behavior change, rehabilitation supporting information) may be provided to the subject. For example, the estimated result may be transmitted to the doctor's terminal device 300 via the interface section 110. This allows the doctor to utilize the estimated results in diagnosing the subject. At this time, similarly to processing 600, for example, information depending on the condition of the subject (for example, information on recommended treatment or intervention, information on recommended rehabilitation) may be provided to the doctor. For example, the estimated result may be sent to the database section 200 via the interface section 110 and stored therein. Thereby, the estimated results can be referenced later or used later to update the learned model or to generate a new learned model.

The processing 700 may be executed by the processor section 120", in which case the results estimated by the processing 700 are used to be analyzed by the analysis means 125. Based on the analysis, the algorithm of the estimation means 123 can be modified by the modification means 126. The processing 700 can be repeated using the modified algorithm.

Figure 7A:
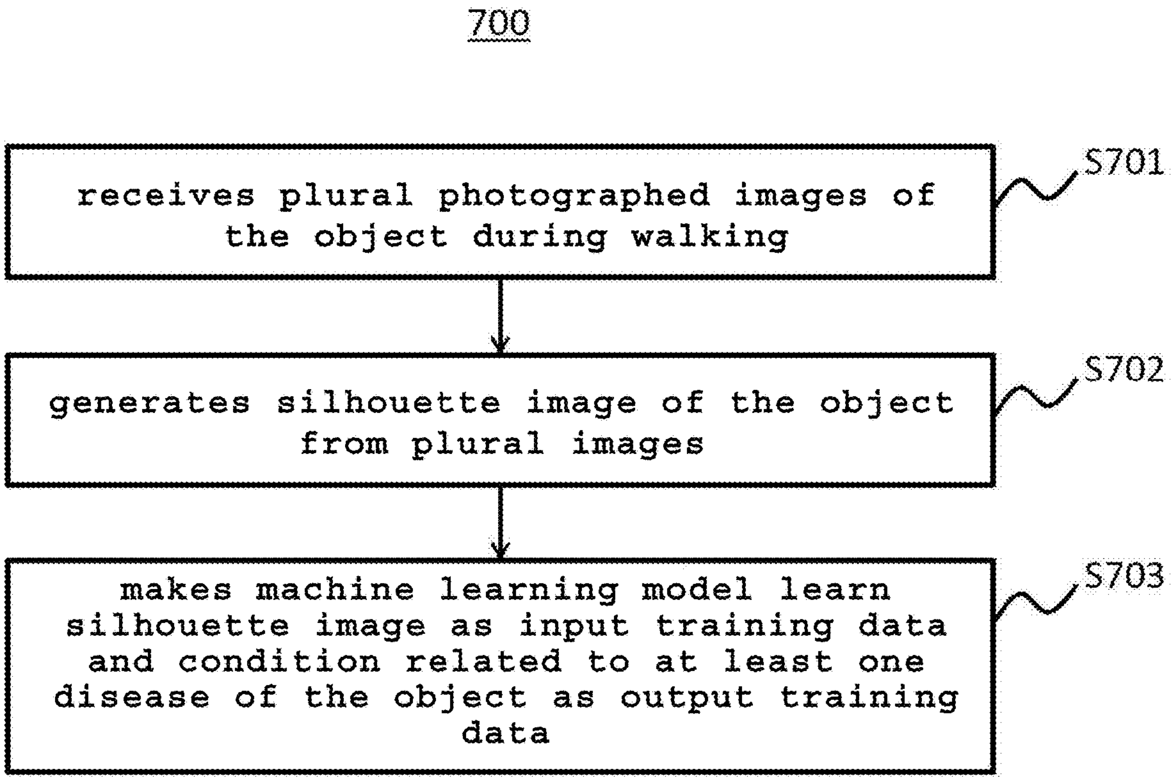
FIG. 7A is a flowchart showing an example of processing (processing 700) by a computer system 100 for estimating a condition of a subject.

FIG. 7A is a flowchart illustrating an example of processing (processing 700) by the computer system 100 for estimating a condition of a subject. The processing 700 is executed by the processor section 140 of the computer system 100. The processing 700 is processing that creates a model for estimating a condition of a subject. The processing 700 may be performed for each of the plurality of objects. That is, by executing the processing 700 once, learning is performed for one object. By performing the processing 700 on multiple objects, learning may be performed on multiple objects. The condition of the subject may be a health-related condition, and the health-related condition includes at least one disease-related condition. In the following explanation, estimating a condition related to at least one disease will be explained as an example, but it is understood that the following processing is also used to estimate other health-related conditions (e.g., estimating walking ability, estimating health level).

In step S701, the receiving means 141 of the processor section 140 receives a plurality of images photographed of an object walking. The plurality of images received by the receiving means 141 are provided to the generation means 142. The receiving means 141 further receives information indicating a condition related to at least one disease of the object. The information indicating a condition related to at least one disease received by the receiving means 141 is provided to the learning means 143.

In step S702, the generation means 142 of the processor section 140 generates at least one silhouette image of the object from the plurality of images received in step S701. The generation means 142 can generate the silhouette image using techniques known in the technical field. The generation means 142 can generate a plurality of silhouette images from a plurality of images, and preferably can generate one silhouette image from a plurality of images.

The generation means 142 can generate at least one silhouette image by, for example, extracting a plurality of silhouette regions from a plurality of images, normalizing the plurality of extracted silhouette regions, and averaging the plurality of normalized silhouette regions. By averaging a plurality of silhouette images, the amount of data can be reduced without significantly impairing the information amount of the silhouette images used.

In step S703, the learning means 143 of the processor section 140 causes a machine learning model to learn at least one silhouette image generated in step S702 as input training data, and a condition related to at least one disease of the object as output training data.

Through the processing 700, learning for one object is completed. By performing the processing 700 on multiple objects, learning is performed on multiple objects and the accuracy of the model may be improved.

The model created by the processing 700 can be used by the processor section 120 or the processor section 120'. Further, the parameters of the learned model created in this way can be stored in the database section 200 or other storage medium.

Figure 7B:
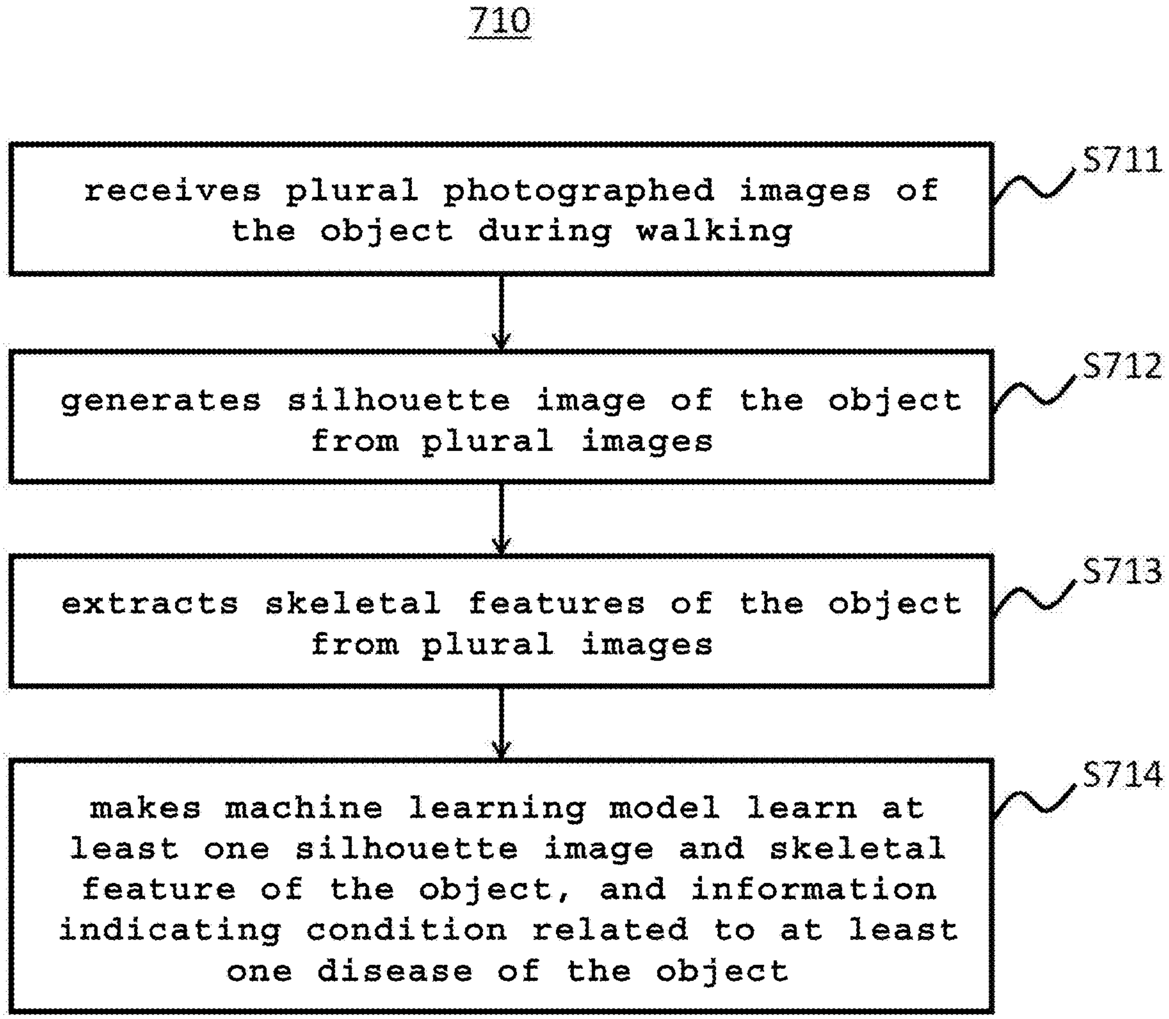
FIG. 7B is a flowchart showing another example of processing (processing 710) by a computer system 100 for estimating a condition of a subject.

FIG. 7B is a flowchart showing another example of the processing (processing 710) by the computer system 100 for estimating a condition of a subject. The processing 710 is performed by processor section 140' of computer system 100. The processing 710 is processing that creates a model for estimating the condition of the subject. The processing 710 may be performed for each of the plurality of objects. That is, by executing the processing 710 once, learning is performed for one object. By performing the processing 710 on multiple objects, learning may be performed on multiple objects. The condition of the subject may be a health-related condition, and the health-related condition includes at least one disease-related condition. In the following explanation, estimating a condition related to at least one disease will be explained as an example, but it is understood that the following processing is also used to estimate other health-related conditions (e.g., estimating walking ability, estimating health level). In the present specification, the disease-related condition includes a condition in which the subject does not actually suffer from the disease (also referred to as "presymptomatic"), and in one embodiment, disease-related conditions may include only conditions in which the object actually suffers from the disease. Therefore, the health-related condition includes a disease-related condition and a condition other than a disease-related condition, and may include either or both of them.

In step S711, the receiving means 141 of the processor section 140' receives a plurality of images photographed of the object walking. Step S711 is similar to step S701. The plurality of images received by the receiving means 141 are provided to the generation means 142. The receiving means 141 further receives information indicating a condition related to at least one disease of the object. The information indicating a condition related to at least one disease received by the receiving means 141 is provided to the learning means 143'.

In step S712, the generation means 142 of the processor section 140' generates at least one silhouette image of the object from the plurality of images received in step S711. Step S712 is similar to step S702.

In step S713, the extraction means 144 of the processor section 140' extracts the skeletal features of the object from the plurality of images received in step S711. The extraction means 144 can generate the silhouette image using techniques known in the art. The extraction unit 144 can generate time-series data of skeletal features by extracting skeletal features from each of the plurality of images.

In step S714, the learning means 143 of the processor section 140' causes a learning model to learn at least one silhouette image generated in step S712 and a skeletal feature extracted in step S713, and information indicating a condition related to at least one disease of the object. For example, the learning means 143 can be configured to cause a first machine learning model to learn at least one silhouette image of the object as input training data and a condition related to at least one disease of the object as output training data, and to cause a second machine learning model to learn a skeletal feature of the object as input training data and a condition related to at least one disease of the object as output training data. Alternatively, for example, the learning means 143 can cause a machine learning model to learn at least one silhouette image and a skeletal feature of the object as input training data, and a condition related to at least one disease the object as output training data.

Through the processing 710, learning for one object is completed. By performing the processing 710 on multiple objects, learning may occur on multiple objects and the accuracy of the model may be improved.

The model created by the processing 710 can be used by the processor section 120 or the processor section 120'. Further, the parameters of the learned model created in this way can be stored in the database section 200 or other storage medium.

In the example described above with reference to FIGS. 6A, FIG. 6B, FIG. 7A, and FIG. 7B, it was explained that each step is executed in a specific order, but the illustrated order is an example, and the order in which each step is executed is not limited to this. Each step can be performed in any order that is logically possible. For example, step S613 can be performed before step S612. For example, step S613 can be performed before step S712.

In the examples described above with reference to FIG. 6A, FIG. 6B, FIG. 7A, and FIG. 7B, although it has been described that the processing of each step shown in FIG. 6A, FIG. 6B, FIG. 7A, and FIG. 7B is realized by the processor section 120 or the processor section 120' or the processor section 140 or the processor section 140' and the program stored in the memory section 130, the present invention is not limited thereto. At least one of the processes in each step shown in FIG. 6A, FIG. 6B, FIG. 7A, and FIG. 7B may be realized by a hardware configuration such as a control circuit.

EXAMPLES

Example 1

A learned model was constructed using a video photographed of subjects with and without spinal stenosis walking. Using the constructed learned model, its performance was evaluated.

(Data Used)

Data from a total of 61 subjects, 49 subjects with spinal stenosis and 12 subjects without spinal stenosis, was used. The 49 subjects with spinal canal stenosis had stenosis somewhere in their spine, and of the 49 subjects with spinal canal stenosis, 42 subjects had Lumbar Pathology and 7 subjects had Cervical Pathology (cervical spine disease).

Here, Lumbar Pathology is a condition in which the lower back (lumbar vertebrae) of the spinal canal is narrowed, resulting in a walking disorder, and is synonymous with LCS. Cervical pathology is a condition in which the cervical region (cervical vertebrae) of the spinal canal is narrowed, resulting in impaired walking, and is synonymous with CSM.

49 subjects were asked to walk 10 meters straight, and their walking was photographed using a camera (USB 3.0 camera FLIR BFLY-U3-13S2 color or USB 3.0 camera FLIR CM3-U3-113S2 color). Among the videos photographed, a video photographed of the subject walking for about 4 m in the middle, excluding the first 3 m and the last 3 m, was used.

Multiple frames were extracted from the video and analyzed as a plurality of images.

(Model Used)

MS-G3D was utilized to predict the presence or absence of spinal canal stenosis based on skeletal features.

ResNet50 was used to predict the presence or absence of spinal canal stenosis based on the silhouette image.

(Evaluation Method)

3-Fold Cross Validation 61 subjects (49 subjects with spinal canal stenosis+12 subjects without spinal canal stenosis) were divided into 3 groups, data from one group was used for evaluation, and data from the remaining two groups was used for learning. Trials were conducted three times by changing the group being evaluated.

(Evaluation of Model for Predicting Presence or Absence of Disease Based on Skeletal Feature)

In the first trial, MS-G3D was caused to learn skeletal features of the subjects in the second group and the third group, and skeletal features of the subjects in the first group were input into the learned MS-G3D, and the accuracy, sensitivity, and specificity of output were calculated.

In the second trial, MS-G3D was caused to learn skeletal features of the subjects in the first group and the third group, and skeletal features of the subjects in the second group were input into the learned MS-G3D, and the accuracy, sensitivity, and specificity of the output were calculated.

In the third trial, MS-G3D was caused to learn skeletal features of the subjects in the first group and the second group, and skeletal features of the subjects in the third group were input into the learned MS-G3D, and the accuracy, sensitivity, and specificity of the output were calculated.

FIG. 8A(a) shows the results. CV1 indicates the result of the first trial. CV2 shows the result of the second trial, and CV3 shows the result of the third trial. Total indicates the average value of CV1 to CV3.

The results of predicting the presence or absence of spinal canal stenosis based on skeletal features had an accuracy of 0.974, a sensitivity of 0.981, and a specificity of 0.880 in terms of average. Moreover, the false positive was 0.019, and the false negative was 0.12. It is considered that the presence or absence of spinal canal stenosis can be predicted with a certain degree of accuracy.

(Evaluation of Model for Predicting Presence or Absence of Disease Based on Silhouette Image)

In the first trial, RESNET 50 was made to learn silhouette images of the subjects in the second group and the third group, and silhouette images of the subjects in the first group were input into the learned RESNET 50, and the accuracy, sensitivity and specificity of the output were calculated.

In the second trial, RESNET 50 was made to learn silhouette images of the subjects in the first group and the third group, and silhouette images of the subjects in the second group were input into the learned RESNET 50, and the accuracy, sensitivity and specificity of the output were calculated.

In the third trial, RESNET 50 was made to learn silhouette images of the subjects in the first group and the second group, and silhouette images of the subjects in the third group were input into the learned RESNET 50, and the accuracy, sensitivity and specificity of the output were calculated.

FIG. 8A(b) shows the results. CV1 indicates the result of the first trial. CV2 shows the result of the second trial, and CV3 shows the result of the third trial. Total indicates the average value of CV1 to CV3.

The results of predicting the presence or absence of spinal canal stenosis based on silhouette images had an accuracy of 0.975, a sensitivity of 0.979, and a specificity of 0.927 in terms of average. Furthermore, the number of false positives was 0.021, and the number of false negatives was 0.073. It was unexpected that the presence or absence of spinal canal stenosis could be predicted with a certain degree of accuracy from silhouette images alone.

(Fusion of Model for Predicting Presence or Absence of Disease Based on Skeletal Feature and Model for Predicting Presence or Absence of Disease Based on Silhouette Image)

In the first trial, MS-G3D was made to learn skeletal features of the subjects in the second and third groups, and RESNET50 was made to learn silhouette images of the subjects in the second and third groups. The skeletal features of each of subjects in the first group of were input into the learned MS-G3D, and the first score was obtained as output. Then, silhouette images of the corresponding subjects in the first group were input into the learned RESNET 50, and the second score was obtained as output. The first score and the second score were added together to obtain the identification result. The accuracy, sensitivity, and specificity of the identification results were calculated.

In the second trial, MS-G3D was made to learn skeletal features of the subjects in the first and third groups, and RESNET50 was made to learn silhouette images of the subjects in the first and third groups. The skeletal features of each of the subjects in the second group were input into the learned MS-G3D and the first score was obtained as output. The silhouette images of the corresponding subjects in the second group were then input into the learned RESNET 50, and the second score was obtained as output. The first score and the second score were added together to obtain the identification result. The accuracy, sensitivity, and specificity of the identification results were calculated.

In the third trial, MS-G3D was made to learn skeletal features of the subjects in the first and second groups, and RESNET50 was made to learn silhouette images of the subjects in the first and second groups. The skeletal features of each of subjects in the third group of were input into the learned MS-G3D, and the first score was obtained as output. The silhouette images of the corresponding subjects in the third group were then input into the learned RESNET 50, and the second score was obtained as output. The first score and the second score were added together to obtain the identification result. The accuracy, sensitivity, and specificity of the identification results were calculated.

FIG. 8A(c) shows the results. CV1 indicates the result of the first trial. CV2 shows the result of the second trial, and CV3 shows the result of the third trial. Total indicates the average value of CV1 to CV3.

The results of predicting the presence or absence of spinal canal stenosis based on skeletal features and silhouette images had an accuracy of 0.995, a sensitivity of 0.999, and a specificity of 0.942, in terms of average. Moreover, the false positive was 0.001, and the false negative was 0.058. Since the features captured in the skeletal features and silhouette images are different, the accuracy is significantly improved by complementary integration. It was unexpected that the presence or absence of spinal canal stenosis could be predicted with extremely high accuracy based on skeletal features and silhouette images.

Example 2

A learned model was constructed using videos photographed of subjects with lumbar canal stenosis and subjects without lumbar canal stenosis walking. Using the constructed learned model, its performance was evaluated. Lumbar spinal canal stenosis refers to a condition of spinal canal stenosis in which the lumbar region is narrowed.

(Data Used)

Data from a total of 61 subjects, 42 subjects with lumbar canal stenosis and 19 subjects without lumbar canal stenosis, was used. Of the 19 subjects without lumbar spinal canal stenosis, 7 had Cervical Pathology (cervical spine disease), and 12 did not have any spinal canal stenosis.

(Method)

Using a video photographed of walking using the same method as in Example 1, multiple frames were extracted from the video and analyzed as a plurality of images.

Using the same model as in Example 1, each model was evaluated using the same evaluation method.

(Evaluation of Model for Predicting Presence or Absence of Disease Based on Skeletal Feature)

As in Example 1, three trials were performed, and the accuracy, sensitivity, and specificity of output were calculated.

The second row of the table in FIG. 8B shows the average value of the results for each trial.

The results of predicting the presence or absence of lumbar canal stenosis based on skeletal features had an accuracy of 0.968, a sensitivity of 0.976, and a specificity of 0.869, in terms of average. Furthermore, the number of false positives was 0.024, and the number of false negatives was 0.131. It is thought that it is possible to predict the presence or absence of a disease with a certain degree of accuracy, even for diseases in the pinpoint region such as the lower back.

(Evaluation of Model for Predicting Presence or Absence of Disease Based on Silhouette Image)

As in Example 1, three trials were performed, and the accuracy, sensitivity, and specificity of output were calculated.

The third row of the table in FIG. 8B shows the average value of the results of each trial.

The results of predicting the presence or absence of lumbar canal stenosis based on silhouette images had an accuracy of 0.968, a sensitivity of 0.976, and a specificity of 0.873, in terms of average. Moreover, the false positive was 0.024, and the false negative was 0.127. It was unexpected that the presence or absence of a disease could be predicted with a certain degree of accuracy from just a silhouette image, even in a pinpoint location such as the lower back.

(Fusion of Model for Predicting Presence or Absence of Disease Based on Skeletal Feature and Model for Predicting Presence or Absence of Disease Based on Silhouette Image)

As in Example 1, three trials were performed, and the accuracy, sensitivity, and specificity of output were calculated.

The fourth row of the table in FIG. 8B shows the average value of the results of each trial.

The results of predicting the presence or absence of lumbar canal stenosis based on skeletal features and silhouette images had an accuracy of 0.986, a sensitivity of 0.994, and a specificity of 0.895, in terms of average. Moreover, the false positive was 0.006, and the false negative was 0.105. Since the features captured in the skeletal features and silhouette images are different, the accuracy is significantly improved by complementary integration. It was unexpected that the presence or absence of lower back disease could be predicted with extremely high accuracy based on skeletal features and silhouette images, even though there was data on subjects with neck disease.

Example 3

A learned model was constructed using videos photographed of subjects with cervical spinal stenosis and subjects without cervical spinal stenosis walking. Using the constructed learned model, its performance was evaluated.

Cervical spinal canal stenosis refers to spinal canal stenosis in which the cervical vertebrae are narrowed.

(Data Used)

Data from a total of 61 subjects, including 7 subjects with cervical spinal stenosis and 54 subjects without cervical spinal stenosis, was used. Of the 54 subjects without cervical spinal canal stenosis, 42 had Lumbar Pathology (lumbar spine disease), and 12 did not have any spinal canal stenosis.

(Method)

Using a video photographed of walking using the same method as in Example 1, multiple frames were extracted from the video and analyzed as a plurality of images.

Using the same model as in Example 1, each model was evaluated using the same evaluation method.

(Evaluation of Model for Predicting Presence or Absence of Disease Based on Skeletal Feature)

As in Example 1, three trials were performed, and the accuracy, sensitivity, and specificity of output were calculated.

The second row of the table in FIG. 8C shows the average value of the results for each trial.

The results of predicting the presence or absence of cervical spinal canal stenosis based on skeletal features had an accuracy of 0.823, a sensitivity of 0.781, and a specificity of 0.888, in terms of average. Moreover, the false positive was 0.219, and the false negative was 0.112. It is thought that it is possible to predict the presence or absence of a disease with a certain degree of accuracy, even for diseases in pinpoint areas such as the cervical vertebrae.

(Evaluation of Model for Predicting Presence or Absence of Disease Based on Silhouette Image)

As in Example 1, three trials were performed, and the accuracy, sensitivity, and specificity of output were calculated.

The third row of the table in FIG. 8C shows the average value of the results of each trial.

The results of predicting the presence or absence of cervical spinal canal stenosis based on silhouette images had an accuracy of 0.818, a sensitivity of 0.776, and a specificity of 0.883, in terms of average. Moreover, the false positive was 0.224, and the false negative was 0.117. It was unexpected that the presence or absence of a disease could be predicted with a certain degree of accuracy from just a silhouette image, even for a disease in a pinpoint location such as the cervical vertebrae.

(Fusion of Model for Predicting Presence or Absence of Disease Based on Skeletal Feature and Model for Predicting Presence or Absence of Disease Based on Silhouette Image)

As in Example 1, three trials were performed, and the accuracy, sensitivity, and specificity of output were calculated.

The fourth row of the table in FIG. 8C shows the average value of the results of each trial.

The results of predicting the presence or absence of cervical spinal canal stenosis based on skeletal features and silhouette images had an accuracy of 0.854, a sensitivity of 0.775, and a specificity of 0.976, in terms of average. Moreover, the false positive was 0.225, and the false negative was 0.024. Since the features captured in the skeletal features and silhouette images are different, the accuracy is significantly improved by complementary integration. As described above, it was unexpected that the presence or absence of a disease could be predicted with a certain level of accuracy based on skeletal features and silhouette images, even though there was data on subjects with lower back disease.

Example 4

The severity of the 29 patients with cervical spondylosis myelopathy was expressed by the Japanese Orthopedic Association Cervical Spine Score (JOA Score: 17 points, with the most severe being 0 points), and the correlation between this score and the estimated score output by the learned model of the present disclosure (called "disease index", the disease index is a variable between 0 and 1, and if it is 0.5 or more, it can be determined that there is a cervical spine disease.) was verified.

Verification was performed by drawing an approximate curve using Excel.

Figure 9:
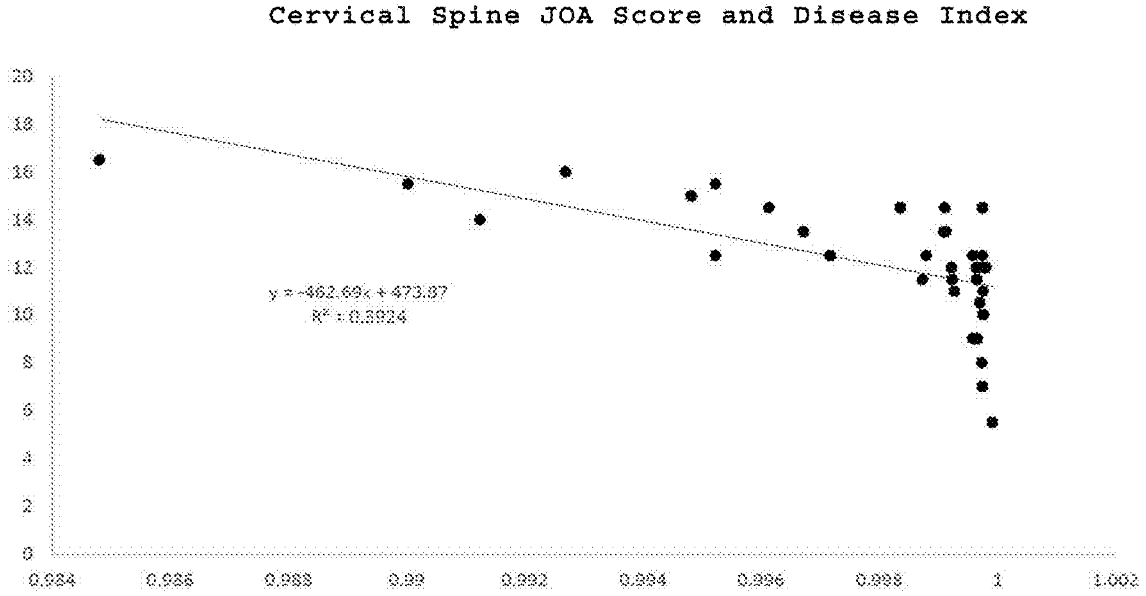
FIG. 9 shows the results of Example 4.
Figure 9:
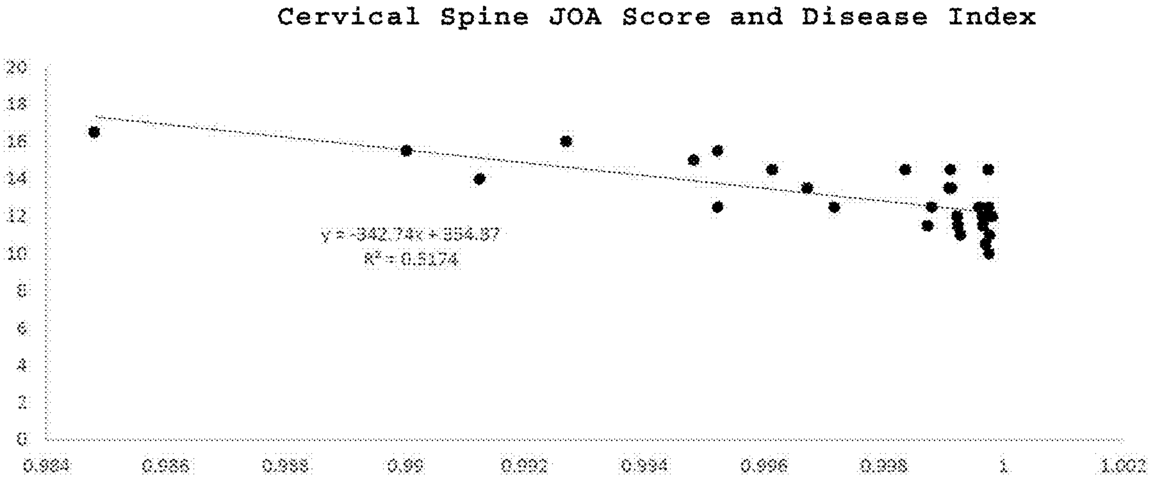

FIG. 9 shows the results of Example 4. FIG. 9(*a*) is a graph showing the correlation between the disease index of 29 subjects and their JOA Score.

As shown in FIG. 9(*a*), when objecting patients with all JOA Scores (mild to severe), a significant correlation was observed between the disease index and JOA Score. In the linear approximation, the coefficient of determination was $R^2=0.39$, which was somewhat low. In the second-order polynomial approximation (not shown), the coefficient of determination was $R^2=0.45$.

The reason for the rather low coefficient of determination is thought to be that the disease index is close to 1 and the distribution of the JOA Score is large. Patients with a JOA Score of 12 or less are suitable for surgery, and patients with a JOA Score of 9 or less are in the most severe condition, and many have strong subjective symptoms and are easy to diagnose, therefore, the present inventors considered that it is more useful to estimate the JOA Score of patients with a JOA Score of 10 or more, rather than estimating the JOA Score of patients with these JOA Scores. This is because diagnosis is not easy in patients with a JOA Score of 10 or more, and it is highly important to monitor whether the disease progresses or recovers.

Therefore, the correlation coefficient was verified for patients with a JOA Score of 10 or more. FIG. 9(*b*) is a graph showing the correlation between the disease index of patients with a JOA Score of 10 or more and each JOA Score.

As shown in FIG. 9(*b*), when objecting patients with a JOA Score of 10 or more, a higher correlation was observed than the results shown in FIG. 9(*a*). In the linear approximation, the coefficient of determination was $R^2=0.51$, which exceeded 0.5. In the second-order polynomial approximation (not shown), the coefficient of determination was $R^2=0.55$. In the fourth-order polynomial approximation (not shown), the coefficient of determination was $R^2=0.57$.

From this result, it was suggested that, when objecting patients with a JOA Score of 10 or more, there is a significantly high correlation between the disease index and the JOA Score, so it is possible to evaluate the JOA Score from the output of the system of the present disclosure.

That is, it has been found that the output of the learned model of the present disclosure can be used as a monitoring index for patients with a JOA Score of 10 or more.

In addition, it was suggested that even in patients with mild symptoms (patients with a JOA Score close to 17), a correlation between the JOA Score and the disease index was observed, so even in patients with mild symptoms to healthy subjects, there is a correlation between the disease index and the JOA Score or other similar scores.

Example 5

For one patient with cervical spondylotic myelopathy (CSM), the walking age was measured using "NEC Walking Posture Measurement System" (https://www.nec-solutioninnovators.co.jp/sl/walkingform/index.html). Measurements were performed over time from before surgery for the treatment of CSM disease to 4 months after surgery (1 point before surgery, 5 points after surgery).

The videos photographed during each measurement were input into the learned model of the present invention, and the disease index was output. The relationship between the walking age and the disease index was verified. Verification was performed by drawing an approximate curve using Excel.

Figure 10:
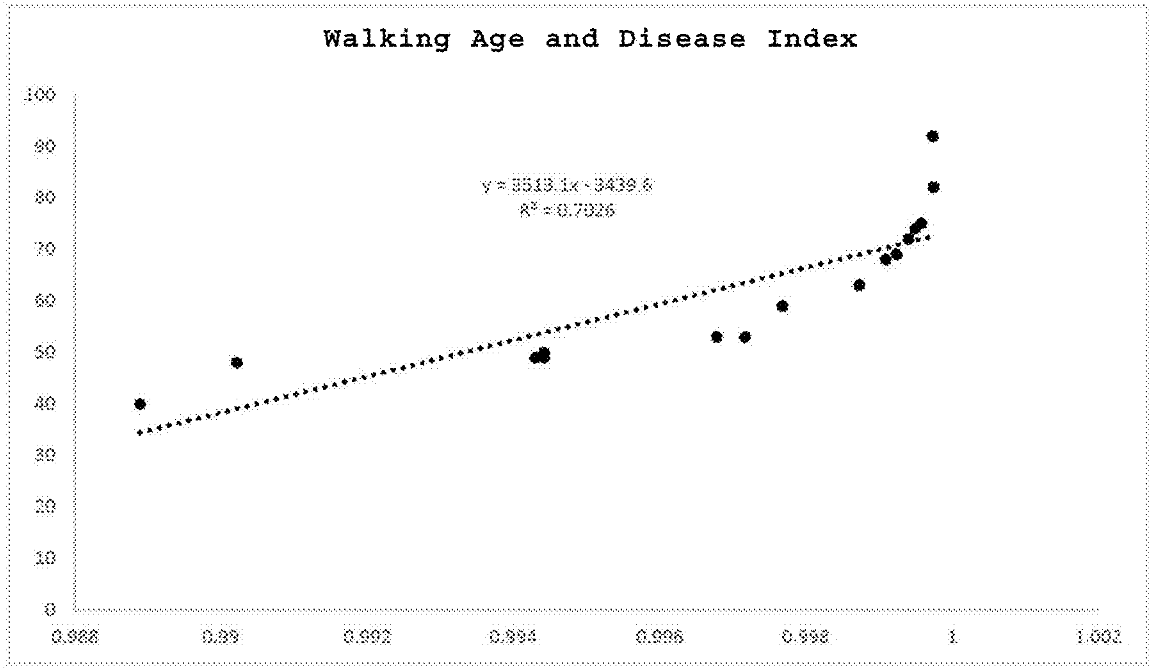
FIG. 10 shows the results of Example 5.

FIG. 10 shows the results of Example 5.

As shown in FIG. 10, a high correlation was observed between the walking age and the disease index. In the linear approximation, the coefficient of determination was $R^2=0.70$.

From this, it can be seen that the disease index output from the learned model of the present disclosure can also be correlated with the index for evaluating the walking ability. It is also understood that the disease index can be utilized to monitor the change in an individual's walking ability over time.

The walking age is known to have good accuracy in adults, especially subjects over 40, preferably over 50, and such monitoring of walking ability over time is preferred for adults, subjects over 40 or over 50.

Hypothetical Example

A silhouette image, which is a multivalued image, is generated using videos photographed of subjects with and without the disease walking, and a learned model is constructed using the silhouette image.

(Data Used)

Multiple subjects with the disease and multiple subjects without the disease were each asked to walk 10 meters in a straight line, and their walking is photographed using a camera. Among the videos obtained, a video photographed of walking about 4 meters in the middle, excluding the first about 3 meters and the last about 3 meters, is used.

A plurality of frames are extracted from the video and analyzed as a plurality of images.

For each subject, a plurality of multivalued silhouette images or one multivalued silhouette image is generated from the plurality of images. In the multivalued silhouette image, each part of the subject is represented by a different pixel.

(Model Used)

ResNet 50 is used to predict the presence or absence of a disease based on a silhouette image.

(Evaluation Method)

3-Fold Cross Validation

A plurality of subjects with a disease and a plurality of subjects without a disease are divided into three groups, data from one group is used for evaluation, and data from the remaining two groups is used for learning. Three trials are conducted by changing the evaluation group.

(Evaluation of Model for Predicting Presence or Absence of Disease Based on Silhouette Image)

In the first trial, RESNET 50 is caused to learn multivalued silhouette images of the subjects in the second group and the third group, and multivalued silhouette images of the subjects in the first group are input into the learned RESNET 50, and the accuracy, sensitivity and specificity of the output are calculated.

In the second trial, RESNET 50 is caused to learn multivalued silhouette images of the subjects in the first group and the third group, and multivalued silhouette images of the subjects in the second group are input into the learned RESNET 50, and the accuracy, sensitivity and specificity of the output are calculated.

In the third trial, RESNET 50 is caused to learn multivalued silhouette images of the subjects in the first group and the second group, and multivalued silhouette images of the subjects in the third group are input into the learned RESNET 50, and the accuracy, sensitivity and specificity of the output are calculated.

It is expected that the prediction accuracy will be improved by using a multivalued silhouette image than when using a binary silhouette image. This is because by using the silhouette features of each part included in the multivalued silhouette image, the amount of information regarding the gait increases (part information is added in addition to the silhouette shape). It should be noted that when multivalued silhouette images are input to a model, the input is complex and the model may be difficult to learn, and errors in generating multivalued silhouette images can have negative effects.

Example 6

For example, the system of the present disclosure having the learned model constructed in the above embodiment is used for rehabilitation guidance in a clinic.

First, at the clinic, the patient is asked to walk and a video is photographed of the patient walking.

When the video photographed is input into the system of the present disclosure, the disease index is output.

A doctor or therapist can determine a rehabilitation menu based on this disease index. For example, a doctor or therapist may determine a rehabilitation menu based on the disease index at that time, may determine a rehabilitation menu based on the rate of change in the disease index, or may determine a rehabilitation menu based on the change over time in the disease index. A doctor or therapist presents a rehabilitation menu to the patient and causes the patient to conduct this menu.

After the patient undergoes a rehabilitation menu for a predetermined period of time, a walking video is photographed again at the clinic and analyzed using the system of the present disclosure. The doctor or therapist can change or adjust the rehabilitation menu based on the disease index at this time. In this way, a rehabilitation menu tailored to the patient's current condition can be provided to the patient.

Example 7

For example, the system of the present disclosure having the learned model constructed in the above embodiment is used for rehabilitation guidance in home medical care.

First, the patient is allowed to walk at home, and the patient is allowed to photograph a video of the walking with the patient's terminal device. At this time, it is preferable to appropriately instruct the photographing conditions.

When a video is photographed, the video photographed is transmitted from the terminal device to the medical facility. The video may be sent directly to the medical facility over a network, or via storage on the cloud, for example. At a medical facility, when a video photographed is input into the system of the present disclosure, the disease index is output.

A doctor or therapist can determine a rehabilitation menu based on this disease index. For example, a doctor or therapist may determine a rehabilitation menu based on the disease index at that time, may determine a rehabilitation menu based on the rate of change in the disease index, or may determine a rehabilitation menu based on the change over time in the disease index. The doctor or therapist presents the determined rehabilitation menu to the patient and has the patient complete it. The determined rehabilitation menu may be directly transmitted to the patient's terminal device via a network, or may be transmitted to the patient's terminal device via a storage on cloud, for example.

The patient is made to perform a rehabilitation menu for a predetermined period of time. The patient is made to photograph a walking video again at the patient's home. Along with video photographing, the patient automatically or manually records the rehabilitation activities that have been performed. When a video is photographed, the video photographed and its recording are transmitted from the terminal device to the medical facility. At a medical facility, when the video photographed is input into the system of the present disclosure, the disease index is output. The doctor or therapist can change or adjust the rehabilitation menu based on the disease index and records at this time. In this way, a rehabilitation menu tailored to the patient's current condition can be provided to the patient. By performing this every day, the doctor or therapist can determine the next day's rehabilitation menu and can provide a rehabilitation menu that suits the patient's current condition.

Example 8

For example, the system of the present disclosure having the learned model constructed in the above embodiment is used for telemedicine.

First, a patient is made to walk in a location remote from a medical facility (for example, at home, on a remote island, or overseas), and the patient is made to photograph a video of the walking with the patient's terminal device. At this time, it is preferable to appropriately instruct the photographing conditions.

When a video is photographed, the video photographed is transmitted from the terminal device to the medical facility. The video may be sent directly to the medical facility over a network, or via storage on the cloud, for example. At a medical facility, when the video photographed is input into the system of the present disclosure, the disease index is output.

A doctor or therapist can determine a rehabilitation menu based on this disease index. For example, a doctor or therapist may determine a rehabilitation menu based on the disease index at that time, may determine a rehabilitation menu based on the rate of change in the disease index, or may determine a rehabilitation menu based on the change over time in the disease index. The doctor or therapist presents the determined rehabilitation menu to the patient and has the patient complete it. The determined rehabilitation menu may be directly transmitted to the patient's terminal device via a network, or may be transmitted to the patient's terminal device via a storage on the cloud, for example.

The patient is made to perform a rehabilitation menu for a predetermined period of time. The patient is made to photograph a walking video again. Along with video photographing, the patient automatically or manually records the rehabilitation activities that have been performed. When a video is photographed, the video photographed and its recording are transmitted from the terminal device to the medical facility. At a medical facility, when the video photographed is input into the system of the present disclosure, the disease index is output. The doctor or therapist can change or adjust the rehabilitation menu based on the disease index and records at this time. In this way, a rehabilitation menu tailored to the patient's current condition can be provided to the patient. By performing this every day, the doctor or therapist can determine the next day's rehabilitation menu and can provide a rehabilitation menu that suits the patient's current condition. Furthermore, even patients located far from medical facilities can receive appropriate treatment or guidance without missing treatment opportunities.

Example 9

For example, the system of the present disclosure having the learned model constructed in the above embodiment is used for health guidance in a shopping mall.

First, participants were asked to walk at a special venue in a shopping mall, and a video was photographed of them as they walked.

When the video photographed is input into the system of the present disclosure, the disease index is output.

A doctor or public health nurse can determine the health condition of the subject based on this disease index. The health condition may be, for example, walking age.

The doctor or public health nurse can provide the subject with the determined health condition and information tailored to the health condition (for example, information that encourages behavior change).

In this way, subjects can be easily motivated to improve their own health in their daily lives.

Example 10

For example, the system of the present disclosure having the learned model constructed in the above embodiment is used for a smartphone information sharing application.

First, the test subject is made to walk at the remote rehabilitation site, and a video is photographed of the process. Based on the video information, parameters such as disease diagnosis name, appropriate rehabilitation prescription example, target load, target number of steps walked, target walking distance, ideal body weight, etc. are presented based on the doctor's instructions (or automatically from the video information).

When the video photographed is input into the system of the present disclosure, the disease index is also output.

The subject uses a smartphone app to share the determined health condition and information tailored to the health condition (for example, information that encourages behavior change) with the test subject's friends, and presents it to a group with the same aspirations, thereby feeling a sense of unity towards achieving the goal.

In this way, subjects can be easily motivated to improve their own health in their daily lives.

The present disclosure is not limited to the embodiments described above. It is understood that the disclosure is to be construed in scope only by the claims. It is understood that those skilled in the art can implement the invention to an equivalent extent based on the description of the present disclosure and common general technical knowledge from the description of the specific preferred embodiments of the present disclosure. It is understood that the patents, patent applications, and publications cited herein should be hereby incorporated by reference to the same extent as if the contents were specifically set forth herein.

INDUSTRIAL APPLICABILITY

The present disclosure is useful as providing a computer system, method, and program for estimating a condition of a subject.

EXPLANATION OF SYMBOLS

100: computer system
110: interface section
120, 120': processor section
121: receiving means
122: generation means
123, 123': estimation means
124: extraction means
130: memory section
140, 140': processor section
141: receiving means
142: generation means
143, 143': learning means
144: extraction means
200: database section
300: terminal device
400: network

The invention claimed is:

1. A computer system for estimating a condition of a subject, wherein the computer system comprises:
one or more processors configured to:
receive a plurality of images photographed of the subject walking,
generate, from each of the plurality of images, a multi-valued silhouette image in which each part of the subject is represented by a different pixel value,
generate a binary silhouette image from each multivalued silhouette image by expressing the different pixel values of the silhouette of the subject with the same pixel value,
generate at least one silhouette image of the subject by extracting silhouette regions from the binary silhouette images, normalizing the extracted silhouette regions, and averaging the normalized silhouette regions, and
estimate a health-related condition of the subject by inputting the at least one silhouette image into a trained machine learning model.

2. The computer system according to claim 1, wherein the one or more processors are further configured to estimate a condition including a condition related to at least one disease of the subject.

3. The computer system according to claim 1, wherein the learned model has learned a relationship between the silhouette image and the condition related to at least one disease of the subject shown in the silhouette image.

4. The computer system according to claim 1, wherein
the one or more processors are further configured to extract a skeletal feature of the subject from the plurality of images, and
estimate the condition further based on the skeletal feature.

5. The computer system according to claim 4, wherein the one or more processors are further configured to
obtain a first score indicating the condition based on the at least one silhouette image,
obtain a second score indicating the condition based on the skeletal feature, and
estimate the condition based on the first score and the second score.

6. The computer system according to claim 1, wherein
the one or more processors are further configured to generate the at least one silhouette image by
extracting a plurality of silhouette regions from the plurality of images,
normalizing each of the plurality of extracted silhouette regions, and
averaging the plurality of normalized silhouette regions.

7. The computer system according to claim 1, wherein the plurality of images are a plurality of frames in a video of the subject walking photographed from a direction approximately perpendicular to the direction in which the subject walks.

8. The computer system according to claim 1, wherein the one or more processors are further configured to
identify, in the silhouette image, a region of interest contributing to the estimation result; and
modify a parameter or structure of an estimation algorithm based on the identified region of interest.

9. The computer system according to claim 1, wherein the health-related condition includes a condition related to at least one disease of the subject, and the at least one disease includes a disease that causes a walking disorder.

10. The computer system according to claim 9, wherein the at least one disease includes at least one selected from the group consisting of locomotor diseases that cause a walking disorder, neuromuscular diseases that cause a walking disorder, cardiovascular disease that cause a walking disorder, and respiratory diseases that cause a walking disorder.

11. The computer system according to claim 9, wherein estimating the condition related to at least one disease includes determining which organ the disease causing a walking disorder relates to.

12. The computer system according to claim 11, wherein the determination includes determining whether the disease causing a walking disorder is a locomotor disease, a neuromuscular disease, a cardiovascular disease, or a respiratory disease.

13. The computer system according to claim 9, wherein the at least one disease includes at least one selected from the group consisting of cervical spondylotic myelopathy (CSM), lumbar canal stenosis (LCS), osteoarthritis (OA), neuropathy, intervertebral disc herniation, ossification of the posterior longitudinal ligament (OPLL), rheumatoid arthritis (RA), heart failure, hydrocephalus, peripheral artery disease (PAD), myositis, myopathy, Parkinson's disease, amyotrophic lateral sclerosis (ALS), spinocerebellar degeneration, multiple system atrophy, brain tumor, Lewy body dementia, subclinical fracture, drug addiction, meniscal injury, ligament injury, spinal cord infarction, myelitis, myelopathy, pyogenic spondylitis, discitis, bunion, chronic obstructive pulmonary disease (COPD), obesity, cerebral infarction, locomotive syndrome, frailty, and hereditary spastic paraplegia.

14. The computer system according to claim 1, wherein the health-related condition of the subject is represented by the severity of at least one disease, and the estimate is the severity.

15. The computer system according to claim 14, wherein the disease is cervical spondylotic myelopathy, and the estimate is a cervical spine JOA score as the severity.

16. The computer system according to claim 15, wherein a plurality of images photographed is received of walking of a subject whose cervical JOA score is determined to be 10 or more.

17. The computer system according to claim 1, wherein the one or more processors are further configured to estimates the walking ability of the subject.

18. The computer system according to claim 17, wherein the walking ability of the subject is expressed by a numerical value indicating which age level the subject is at.

19. The computer system according to claim 1, wherein the one or more processors are further configured to provide treatment or intervention or information according to the estimated condition.

20. A method for estimating a condition of a subject, wherein the method comprises:

receiving a plurality of images photographed of the subject walking, generating, from each of the plurality of images, a multivalued silhouette image in which each part of the subject is represented by a different pixel value, generating a binary silhouette image from each multivalued silhouette image by expressing the different pixel values of the silhouette of the subject with the same pixel value, generating at least one silhouette image of the subject extracting silhouette regions from the binary silhouette images, normalizing the extracted silhouette regions, and averaging the normalized silhouette regions, and estimating a health-related condition of the subject by inputting the at least one silhouette image into a trained machine learning model.

21. A method that creates a model for estimating a condition of a subject, wherein the method comprises:

receiving a plurality of images photographed of the subject walking, generating, from each of the plurality of images, a multivalued silhouette image in which each part of the subject is represented by a different pixel value, generating a binary silhouette image from each multivalued silhouette image by expressing the different pixel values of the silhouette of the subject with the same pixel value, generating at least one silhouette image of the subject extracting silhouette regions from the binary silhouette images, normalizing the extracted silhouette regions, and averaging the normalized silhouette regions, and causing a machine learning model to learn the at least one silhouette image as input training data and the health-related condition of the subject as output training data, for each subject among a plurality of subjects.

* * * * *